US008217075B2

(12) United States Patent
Pachot et al.

(10) Patent No.: US 8,217,075 B2
(45) Date of Patent: Jul. 10, 2012

(54) 2-AMINO-2-PHENYL-ALKANOL DERIVATIVES, THEIR PREPARATION AND PHARMACEUTICAL COMPOSITIONS CONTAINING THEM

(75) Inventors: Jean Pachot, La Varenne (FR); Christophe Dini, Le Plessis Pate (FR); Alexis Denis, Paris (FR)

(73) Assignee: Oroxcell, Romainville (FR)

( * ) Notice: Subject to any disclaimer, the term of this patent is extended or adjusted under 35 U.S.C. 154(b) by 632 days.

(21) Appl. No.: 12/360,306

(22) Filed: Jan. 27, 2009

(65) Prior Publication Data
US 2009/0197924 A1  Aug. 6, 2009

Related U.S. Application Data

(60) Provisional application No. 61/084,829, filed on Jul. 30, 2008.

(30) Foreign Application Priority Data

Jan. 31, 2008   (FR) ..................................... 08 00521

(51) Int. Cl.
*A61K 31/27* (2006.01)
*A61K 31/235* (2006.01)
*A61K 31/24* (2006.01)
*C07C 261/00* (2006.01)
*C07C 69/00* (2006.01)

(52) U.S. Cl. .......... 514/534; 514/486; 514/533; 560/27; 560/64

(58) Field of Classification Search .................. 514/486, 514/533, 534; 560/27, 61, 64
See application file for complete search history.

(56) References Cited

U.S. PATENT DOCUMENTS 5,326,878 A  7/1994 Depernet et al.

FOREIGN PATENT DOCUMENTS

| EP | 0 510 168 | 10/1992 |
|---|---|---|
| EP | 1 110 549 | 6/2001 |
| FR | 2 765 218 | 12/1998 |
| GB | 1 434 826 | 5/1976 |
| WO | WO 99/01417 | 1/1999 |
| WO | WO 2007/140611 | 12/2007 |

OTHER PUBLICATIONS

Martin, Arnaud et al.; "Synthesis of Methylamino-2-Phenyl-2-Butyl-3,4,5-Trimethoxybenzoate, The Main Bioactive Metabolite of Trimebutine Maleate;" Arzneimittel-Forschung, 50(I), No. 6, XP-001538217, 2000; pp. 544-549.

Fiaux, Hélène et al.; "Pyrrolidine Derivatives as New Inhibitors of ∝—Mannosidases and Growth Inhibitors of Human Cancer Cells;" Laureates: Awards and Honors SCS Fall Meeting 2005, and Chimia 60, No. 4, 2006; XP-002478240 and XP-002478241; 7 pages.

Langlois, Annik et al.; "Fedotoxine Blocks Hypersensitive Visceral Pain in Conscious Rats: Action at Peripheral κ-Opioid Receptors;" European Journal of Pharmacology, 324, 1997; pp. 211-217.

Wheeler-Aceto Helen et al.; "Standardization of the Rat Paw Formalin Test for the Evaluation of Analgesics;" Psychopharmacology, 104, 1991; pp. 35-44.

Brown, George B. "$^3$H-Batrachotoxinin-A Benzoate Binding to Voltage-Sensitive Sodium Channels: Inhibition by the Channel Blockers Tetrodotoxin and Saxitoxin;" The Journal of Neuroscience, vol. 6, No. 7, Jul. 1986; pp. 2064-2070.

*Primary Examiner* — Taylor Victor Oh
(74) *Attorney, Agent, or Firm* — Harness, Dickey & Pierce, P.L.C.

(57) ABSTRACT

2-amino-2-phenyl-alkanol ester derivatives of general formula (I) in which: $R_1$ is H, straight or branched 1 to 4C alkyl, straight or branched 2 to 4C alkyl substituted by OH, alkoxy, alkylthio, acyloxy, NH2, alkylamino, dialkylamino, alkylcarbamoyloxy, alkoxycarbonylamino, ureido or alkylureido, $R_2$ is a —CO—R radical in which R is H, alkyl, aryl, heterocyclyl, benzyl or heterocyclylmethyl, or $R_2$ is a —CO—Y—$R_4$ radical for which Y is —O—, —S—, —NH—, -Nalk- for which alk is straight or branched (1 to 4C) alkyl, and $R_4$ is alkyl, aryl, aralkyl or heterocyclylalkyl, capable of being substituted by one or more halogen atoms or OH radicals, straight or branched (1 to 4C) alkyl, alkoxy, alkylthio, acylaminoalkylthio, alkoxycarbonyl or acylamino (1 to 4C) straight or branched, or oxo, or capable of being substituted by $R_5$COO— in which $R_5$ is alkyl optionally substituted by benzyloxycarbonylamino, acylamino or by an amino acid residue, or represents an heterocyclyl radical, or $R_2$ is alkyl (2 to 4C) substituted by OH, alkoxy, alkylthio, acyloxy, NH2, alkylamino, dialkylamino optionally forming, with the nitrogen atom to which they are attached, a 5- or 6-member heterocycle optionally having another heteroatom (O or N), or substituted by alkylcarbamoyloxy, alkoxycarbonylamino, ureido or alkylureido, it being understood that said straight or branched substituted alkyl radical comprises at least 2C between >N—$R_2$ and the substituent; and $R_3$ is alkyl (1 to 4C) straight or branched unless specifically mentioned, alkyl or acyl are straight or branched (1 to 7C), in their R or S forms or their mixtures, as well as their pharmaceutically acceptable salts when these exist.

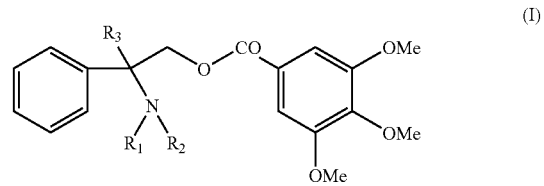

(I)

14 Claims, No Drawings

2-AMINO-2-PHENYL-ALKANOL DERIVATIVES, THEIR PREPARATION AND PHARMACEUTICAL COMPOSITIONS CONTAINING THEM

CROSS-REFERENCE TO RELATED APPLICATIONS

This application claims priority to U.S. Provisional Application Ser. No. 61/084,829, filed Jul. 30, 2008. This application also claims priority to French application Ser. No. 08/00521, filed Jan. 31, 2008. Both of these applications are incorporated by reference herein.

BACKGROUND AND SUMMARY

The present invention relates to variously-substituted 2-amino-2-phenyl-alkanol derivatives which are particularly useful especially for their analgesic action. The present invention also relates to the preparation of these derivatives as well as the pharmaceutical compositions containing them.

(S) 2-methylamino-2-phenyl-n.butyl 3,4,5-trimethoxy benzoate and its use in the treatment of chronic pain have been described in international application WO 99/01417. The use of trimebutine 2-dimethylamino-2-phenylbutyl-3,4,5-trimethoxy-benzoate hydrogen maleate or its stereoisomers in the treatment of inflammatory disorders and pain have been described in European application EP 1,110,549. Esters of amino alcohols with the following structure have been described in UK Patent Application GB 1,434,826:

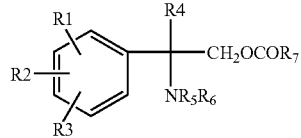

in which $R_1$ to $R_3$ can be in particular a hydrogen atom, $R_4$ can be an alkyl radical, $R_7$ can be aryl optionally substituted by 1 to 3 alkoxy radicals and $R_5$ and $R_6$ represent a hydrogen atom, an alkyl or aralkyl radical or form a heterocycle together with the nitrogen atom to which they are attached. The products are useful as anti-spasmodic agents. The UK application also describes carbamates for which $R_7$ has the structure —NH—$R''_7$. The arylcarbamates thus constituted have analgesic and anti-inflammatory activity. However, the modifications made to the amine were quite limited and were unable to lead to powerful analgesics.

It has now been found that 2-amino-2-phenyl-alkanol ester derivatives of general formula:

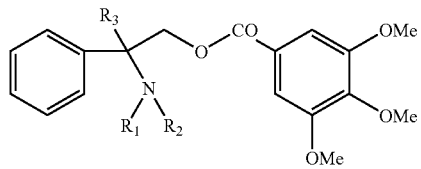

in which:

$R_1$ is a hydrogen atom, an alkyl radical containing 1 to 4 carbon atoms in a straight or branched chain, an alkyl radical containing 2 to 4C in a straight or branched chain substituted by hydroxy, alkoxy, alkylthio, acyloxy, amino, alkylamino, dialkylamino, alkylcarbarnoyloxy, alkoxycarbonylamino, ureido or alkylureido, $R_2$ is a —CO—R radical in which R is a hydrogen atom, an alkyl radical, an aryl, heterocyclyl, benzyl or heterocyclylmethyl radical, a —CO—Y—$R_4$ radical for which Y is a heteroatom chosen from —O—, —S—, —NH—, -Nalk- for which alk is a straight or branched alkyl radical containing 1 to 4C, and $R_4$ is chosen from the alkyl, aryl, aralkyl or heterocyclylalkyl radicals, capable of being substituted by one or more halogen atoms or hydroxy, alkyl radicals containing from 1 to 4 C in a straight or branched chain, alkoxy, alkylthio, acylaminoalkylthio, alkoxycarbonyl or acylamino the alkyl residues of which contain 1 to 4C in a straight or branched chain, or oxo, or capable of being substituted by an $R_5$COO-radical in which $R_5$ is an alkyl radical optionally substituted by benzyloxycarbonylamino, acylamino or by an amino acid residue, or represents an heterocyclyl radical, or $R_2$ is an alkyl radical containing 2 to 4C substituted by hydroxy, alkoxy, alkylthio, acyloxy, amino, alkylamino, dialkylamino the alkyl residues of which can form, with the nitrogen atom to which they are attached, a heterocycle having 5 or 6 members, optionally bearing another heteroatom chosen from oxygen or nitrogen, or substituted by alkylcarbamoyloxy, alkoxycarbonylamino, ureido or alkylureido, it being understood that said substituted alkyl radical is in a straight or branched chain and comprises at least 2 carbon atoms between the nitrogen atom bearing $R_2$ and the substituent;

$R_3$ is an alkyl radical containing 1 to 4 carbon atoms in a straight or branched chain, in their R or S forms or their mixtures, as well as their pharmaceutically acceptable salts, when these exist, have a particularly useful activity as analgesics, in particular in the treatment of chronic pain.

It is understood that unless specifically mentioned, the alkyl or acyl radicals or residues are straight or branched and contain 1 to 7 carbon atoms, in particular the acyl radicals can be acetyl radicals. The aryl or aralkyl radicals can be mono or bicyclic radicals, comprising 6 to 10 members, for example phenyl, naphthyl, benzyl, phenethyl or naphthylalkyl. It is understood that the heterocyclyl radicals can be mono or bicyclic radicals, aromatic or not, comprising 5 to 10 members and containing 1 to 4 heteroatoms chosen from oxygen, nitrogen or sulphur. In particular they can be chosen from thienyl, furyl, pyrrolyl, pyrrolidinyl piperidyl pyridyl, pyrazinyl, pyrimidinyl, pyridazinyl, piperazinyl, dioxolyl, imidazolyl, imidazolinyl, pyrazolyl, tetrazolyl, pyrannyl, tetrahydropyrannyl, tetrahydrofuranyl, oxazolyl, thiazolyl, thiazinyl, morpholinyl, thiomorpholinyl, indolyl, indolizinyl, quinolyl, naphthyridinyl radicals. It is understood that the amino acids mentioned above can be in particular chosen from glycine, alanine, leucine, isoleucine, proline, valine, phenylalanine in the L or D series and that these groups are protected prior to the synthesis reactions, in the form of amides or carbamates; the protection and the release of the protective radicals is carried out according to the methods described by T. W. Greene and P. G. M. Wuts, Protective Groups in Organic Synthesis, 4th Edition ISBN 978-0-471-69754-1, December 2006. The halogen atoms are chosen from chlorine, fluorine, bromine and iodine.

According to a preferred embodiment of the invention, the alkyl or acyl radicals are straight or branched and contain 1 to 4 carbon atoms. According to the invention, the 2-amino-2-phenyl-alkanol ester derivatives of general formula (I) are prepared by the action of a derivative of general formula:

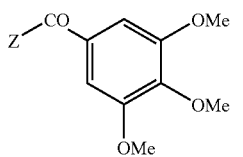
(II)

in which Z is a halogen atom, a hydroxy radical or the residue of a reactive ester, on the derivative of 2-amino-2-phenyl alkanol of general formula:

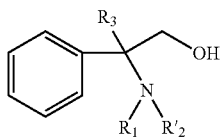
(III)

in which $R_1$ and $R_3$ are defined as previously and $R'_2$ is a hydrogen atom or is defined as $R_2$ previously, followed if appropriate, when one of $R'_2$ or $R_1$ is the hydrogen atom, by substitution of the amine of the 2-amino-2-phenyl-alkanol ester derivative obtained, of general formula:

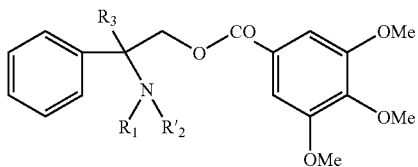
(IV)

in which $R_1$ and $R'_2$ and $R_3$ are defined as above.
either, when $R'_2$ is H, and if it is desired to obtain derivatives for which $R_2$ is —CO—R, by the action of a reactive derivative of the acid of general formula

R—COOH (V)

in which R is defined as previously,
or, when $R'_2$ is H, and it is desired to obtain derivatives for which $R_2$ is —CO—Y—$R_4$, Y being O, S, NH or Nalk
either, by the action of phosgene, followed by the reaction with the alcohol, the thiol or the amine of general formula:

$R_4$—YH (VI)

in which $R_4$ is an optionally-substituted alkyl radical and where if appropriate the functions which can be altered in the reaction are previously protected, or an aryl, aralkyl or heterocyclylalkyl radical, and Y is the oxygen or sulphur atom, or a NH or Nalk radical
or, by the action of the halide of general formula:

$R_4$—Y—COHal (VII)

in which $R_4$ is defined as previously, preferably branched aryl or alkyl, Y is the oxygen or sulphur atom and Hal is a halogen atom, preferably chlorine,
or, when it is desired to obtain an $R_4$ radical bearing the —C(alk)-O—CO—$R_5$ substitution for which alk is defined as in claim 2 and $R_5$ is defined as in claim 1, by the action of chloroalkylchloroformate, followed by reacting the product obtained with an alkaline salt of the corresponding acid $R_5$COOH, for example the sodium salt, potassium salt or the caesium salt of the corresponding acid: $R_5$COOCs, or alternatively the silver salt or the quaternary ammonium salt (for instance the tert-butyl ammonium salt) of said acid.
either, when $R'_2$ is H, and if it is desired to obtain derivatives for which $R_2$ is substituted alkyl, or when a derivative of general formula (IV) has been obtained, for which $R_1$ is a hydrogen atom and $R'_2$ is defined as $R_2$, and if it is desired to obtain a product of general formula (I) for which $R_1$ is alkyl optionally substituted, by acylation by an acid halide or a reactive ester of structure:

$R_2$—CO-Z (VIIIa)

or $R_1$—CO-Z (VIIb)

in which $R_1$ or $R_2$ are defined as above and Z is a halogen atom or the residue of a reactive ester, followed by reducing the amide formed to an amine.
or also, when a derivative of general formula (IV) has been obtained for which $R_1$ is a hydrogen atom and $R'_2$ is defined as $R_2$, and if it is desired to obtain a product of general formula (I) for which $R_1$ is alkyl, by the action of a halogenated derivative of formula $R_1$—X (IX)

in which $R_1$ is an alkyl radical and X is a halogen atom or a sulphonic radical, in the presence of a base.

The product of general formula (II) can be a reactive 3,4,5-trimethoxy benzoic acid derivative, such as an acid halide or a reactive ester. The reaction of the 2-amino-2-phenyl alkanol derivative of general formula (II) is carried out preferably using a derivative for which $R'_2$ is the hydrogen atom. When the product of general formula (II) is a reactive derivative of 3,4,5-trimethoxy benzoic acid such as the acid halide or a reactive ester, the reaction of the derivative of general formula (II) with the 2-amino-2-phenyl alkanol derivative of general formula (III) is carried out advantageously in the presence of a nitrogenous base such as for example triethylamine, dimethylaminopyridine, diisopropylethylamine in the case of the acid halide of formula (II) and the reaction is generally carried out in an organic solvent such as a chlorinated solvent (dichloromethane, dichlorethane, chloroform for example), at a temperature comprised between 0 and 70° C., preferably operating under nitrogen. And in the case of a reactive ester of formula (II), in the presence of sodium methylate in an organic solvent such as toluene in the presence of an alcohol such as methanol or ethanol, at a temperature comprised between 25 and 150° C.

When Z is a halogen atom, it is advantageously chosen from chlorine or bromine. When the product of general formula (II) is 3,4,5-trimethoxy benzoic acid, the reaction is generally carried out in the presence of a carbodiimide, in a halogenated solvent (dichloromethane, dichlorethane, chloroform for example), at a temperature comprised between 0 and 70° C. It is understood that when it is desired to obtain a derivative of general formula (IV) in R or S form, a derivative of 2-amino-2-phenyl alkanol of general formula (III) in R or S form is reacted. It is also understood that the derivatives of general formula (IV) in R or S form lead to derivatives of general formula (I) in R or S form.

The substitution of the amine of the derivative of general formula (IV) by the action of a reactive derivative of the acid of general formula (V) is advantageously carried out using the acid halide or an ester, in particular reactive ester, preferably in the presence of a condensation agent such as a tertiary amine (triethylamine, diisopropylethylamine, dimethylaminopyridine in particular). The reaction is generally carried out in an organic solvent such as a chlorinated solvent (dichloromethane, dichlorethane, chloroform for example), at a temperature comprised between 0 and 70° C. When it is desired to obtain the derivative for which $R_2$ is formyl, the operation is advantageously carried out by the action of an ester, dispensing with the use of a solvent.

The reaction of the alcohol or thiol of general formula (VI) is carried out after the action of phosgene on the amine of the derivative of general formula (IV), (in the form of a solution in an aromatic solvent such as for example toluene), in an organic solvent such as a halogenated solvent (for example chlorinated solvent such as dichloromethane, dichlorethane or chloroform) in the presence of a tertiary amine (triethylamine, diisopropylethylamine, dimethylaminopyridine in particular) at a temperature comprised between 0 and 25° C. The reaction of the alcohol or the thiol of general formula (VI) is carried out by the addition of the derivative of general formula (VI) in the presence of a tertiary amine as mentioned above, at a temperature comprised between 0 and 70° C., in a halogenated solvent (dichloromethane, dichlorethane, chloroform for example). Preferably operating under nitrogen. It is understood that when substituents are at risk of being altered during the course of the reaction, the latter are protected beforehand. The protection and release of the protective radicals is carried out according to the methods described by T. W. Greene and P. G. M. Wuts, Protective Groups in Organic Synthesis, 4th Edition ISBN 978-0-471-69754-1, December 2006.

The reaction of the derivative of general formula (VII) with the amine of the derivative of general formula (IV) is carried out in the presence of a condensation agent such as a tertiary amine (triethylamine, diisopropylethylamine, dimethylaminopyridine in particular). The reaction is generally carried out in an organic solvent such as a chlorinated solvent (dichloromethane, dichlorethane, chloroform for example), or tetrahydrofuran, at a temperature comprised between 0 and 70° C. Preferably the operation is carried out under nitrogen. When it is desired to obtain a compound in which the $R_4$ radical have the —C(alk)-O—CO—$R_5$ substitution, the reaction is carried out through the action of the chloroalkylchloroformate on the compound of the general formula (IV), and the reaction is conducted in an organic solvent such as a chlorinated solvent (dichloromethane, dichlorethane for example), or such as an ether (tetrahydrofuran for example), at a temperature of between −10 and 50° C. It is followed by the reaction of the obtained compound with an alkaline salt of the corresponding acid $R_5COOH$, for example the sodium salt, the potassium salt or the caesium salt, the silver salt or the quaternary ammonium salt, in an organic solvent such as, for instance an amide such as dimethylformamide, a chlorinated solvent (dichloromethane for instance), an ester (ethyl acetate for instance), an aromatic hydrocarbon (toluene for example), a nitrile (acetonitrile for example), a ketone (acetone, methyl ethyl ketone for example), optionally in the presence of sodium iodide, at a temperature of between 0 and 60° C.

When it is desired to obtain a compound of the general formula (I) in which $R_2$ is a substituted alkyl or in which $R_1$ is an optionally substituted alkyl, the alkylation reaction of the amine of the derivative of general formula (IV) is carried out in a halogenated solvent (dichloromethane, dichlorethane for example) or in an ether (tetrahydrofuran), at a temperature comprised between 0 and 70° C. If necessary, the reactive ester can be prepared using hydroxybenzotriazole. The reduction is carried out in the presence of borane in tetrahydrofuran, at a temperature comprised between 0 and 70° C. The reaction of the product of formula (IX) is carried out using a halogenated derivative for which the halogen is chosen from chlorine, bromine or iodine or using a sulphonic derivative such as tosylate, mesylate or triflate, in the presence of a base such as an alkaline carbonate ($NaHCO_3$ or $KHCO_3$ for example).

The derivatives of 3,4,5-trimethoxy benzoic acid of general formula (II) can be prepared according to the usual methods for the conversion of carboxylic acids to their reactive derivatives which do not change the remainder of the molecule. The derivatives of general formula (III) can be prepared according to the method described in patent applications FR 2,765,218 or EP 510,168, or by analogy with the method described in these applications. The halogenated derivatives of general formula (VII) can be prepared by the action of phosgene on the corresponding alcohol or thiol of general formula (VI). The operation is carried out under conditions analogous to the conditions described previously for the action of phosgene on the amine of the derivative of general formula (IV). It is understood that when it is desired to obtain a product of general formula (I) in S or R form, a derivative of 2-amino-2-phenyl alkanol of general formula (III) in S or R form is reacted.

The 2-amino-2-phenyl alkanol derivatives of general formula (III) in S or R form can be prepared according to the method described in European patent EP 510,168 or by separation according to the usual methods for the separation of enantiomers which do not affect the remainder of the molecule. When they exist, the pharmaceutically acceptable salts can be addition salts with acids. In particular salts with mineral acids such as for example hydrochlorides, the hydrobromides, sulphates, phosphates or addition salts with organic acids such as for example acetates, maleates, fumarates, tartrates, citrates. The derivatives of general formula (I) can be purified according to the usual methods, in particular by chromatography or by crystallization. The derivatives of general formula (I) are particularly useful due to their powerful analgesic activity, in particular in chronic pain. Their activity has been demonstrated in vitro in the test of the inhibition of the sodium channels by application of the method of G. B. Brown, $^3$H-batrachotoxinin-A benzoate binding to voltage-sensitive sodium channels: inhibition by the channel blockers tetrodotoxin and saxitoxin, J. Neurosci., 6, 2064 (1986). In vitro in this test, the products according to the invention have demonstrated inhibition activities between 25 and 90% for concentrations of 3.2 (M).

Moreover, in vivo their activity has been demonstrated in the rat in the test of formalin-induced short- and long-phase pain, adapted from the method of Wheeler-Aceto et al., psychopharmacology, 104, 35-44 (1991). In this method the product of Example 4 demonstrated short- and long-phase activity at the dose of 39.3 mg/kg by subcutaneous route. In vivo activity has also been demonstrated in the abdominal pain test, by irritation and distension of the colon in rats according to the method adapted from the method described by Langlois et al., Euro. J. Pharmacol., 324, 211-217 (1997). In this test the product of Example 4 demonstrated activity in rats from 13.1 mg/kg and at doses of 26.2 mg/kg by subcutaneous route. Furthermore, it has been demonstrated, after i.v. injection in rats, that the half-life times of certain products according to the present invention are particularly high. Finally, the products according to the invention do not show toxicity. In fact, in the mouse by intraperitoneal route at doses of 26.2 mg/kg in 7 administrations repeated over 2 days and in the rat by oral route at 39.3 mg/kg, no mortality and no sign of abnormal behaviour were observed.

DETAILED DESCRIPTION

Particularly useful are the products of general formula (I) hereafter called (Ia) for which $R_1$ and $R_3$ are defined as previously and $R_2$ in $-NR_1R_2$ is a $-CO-O-R_4$ radical for which $R_4$ has a structure:

$$-C(alk)-O-CO-R_5 \qquad (X)$$

alk being an alkyl radical containing 1 to 6 carbon atoms in a straight or branched chain and $R_5$ is defined as in general formula (I), or hereafter called (Ia') for which $R_3$ is defined as previously and in $-NR_1R_2$, $R_1$ is a hydrogen atom and $R_2$ is a $-CO-R$ radical as defined previously. And from the products of general formula (Ia) and (Ia') the products of general formula (Ia) are more particularly preferred for which $R_1$ is a hydrogen atom, an alkyl radical containing 1 to 4 carbon atoms (in particular methyl) or a 2-methoxyethyl radical. Also preferred are the products of general formula (I), hereafter called (Ib), for which $R_1$ and $R_3$ are defined as previously and $R_2$ in $-NR_1R_2$ is a substituted alkyl radical as defined previously for $R_2$ in general formula (I).

EXAMPLES

The following examples illustrate the present invention. In the examples which follow, the abbreviations used have the following meaning:
DMF dimethylformamide
DMSO dimethylsulphoxide
THF tetrahydrofuran
DIPEA N,N-diisopropylethylamine
TLC thin layer chromatography

Example 1

ORC012

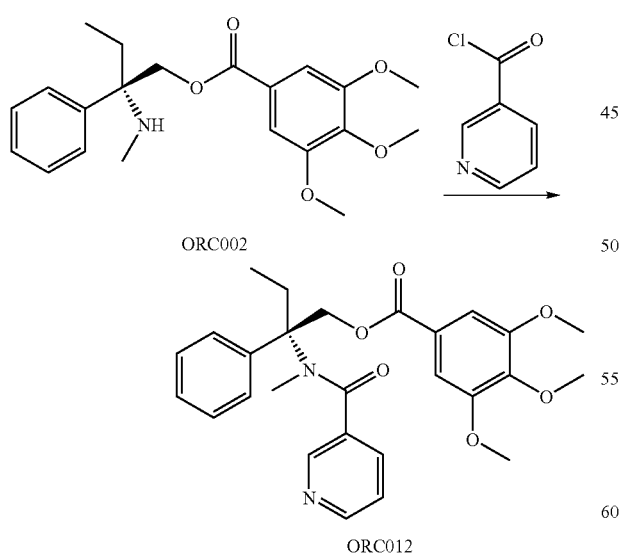

0.300 g (0.8 mmol, 1 eq.) of (S) 2-methylamino-2-phenyl-n-butyl 3,4,5-trimethoxybenzoate and 0.442 g (2.4 mmol, 3 eq.) of nicotinoyl chloride hydrochloride are placed under nitrogen then suspended in 3 ml of dry 1,2-dichloroethane. Then 0.4 ml (2.4 mmol, 3 eq.) of N,N-diisopropylethylamine is added. Stirring is maintained for 20 hours at ambient temperature.

The reaction mixture is treated with 6 ml saturated $NaHCO_3$ then extracted with 12 ml dichloromethane. The organic phase is washed again with 6 ml saturated $NaHCO_3$ then dried over $Na_2SO_4$, filtered and evaporated to dryness. The residue obtained is purified by flash chromatography on silica gel (ethyl acetate/cyclohexane gradient 3:7 to 6:4, v/v) in order to produce 0.189 g (46%) of the expected product (S) 2-(methyl 3-pyridylcarbonyl amino)-2-phenyl-n-butyl 3,4,5-trimethoxybenzoate in the form of a white foam.

$^1$H-NMR ($CDCl_3$, 400 MHz):
δ (ppm)=0.93 (t, J=7.6 Hz, 3H, $CH_3$); 2.27 (m, 1H, diastereotopic $CH_2$); 2.52 (m, 1H, diastereotopic $CH_2$); 2.91 (s, 3H, $NCH_3$); 3.77 (s, 6H, 2×$OCH_3$); 3.82 (s, 3H, $OCH_3$); 5.03 (d, J=11.5 Hz, 1H, $OCH_2$); 5.24 (d, J=11.5 Hz, 1H, $OCH_2$); 7.10-7.40 (m, 8H, ArH); 7.73 (d, J=7.8 Hz, 1H, ArH); 8.57 (d, J=4.9 Hz, 1H, ArH); 8.66 (m, 1H, ArH). LC-MS (ES): m/z=479 (M+H)$^+$. $R_f$ ($SiO_2$, dichloromethane/methanol 98:2): 0.36.

(S) 2-methylamino-2-phenyl-n-butyl 3,4,5-trimethoxybenzoate can be prepared according to the method described in applications FR 2,765,218 and EP 0510,168.

Example 2

Synthesis of ORC011

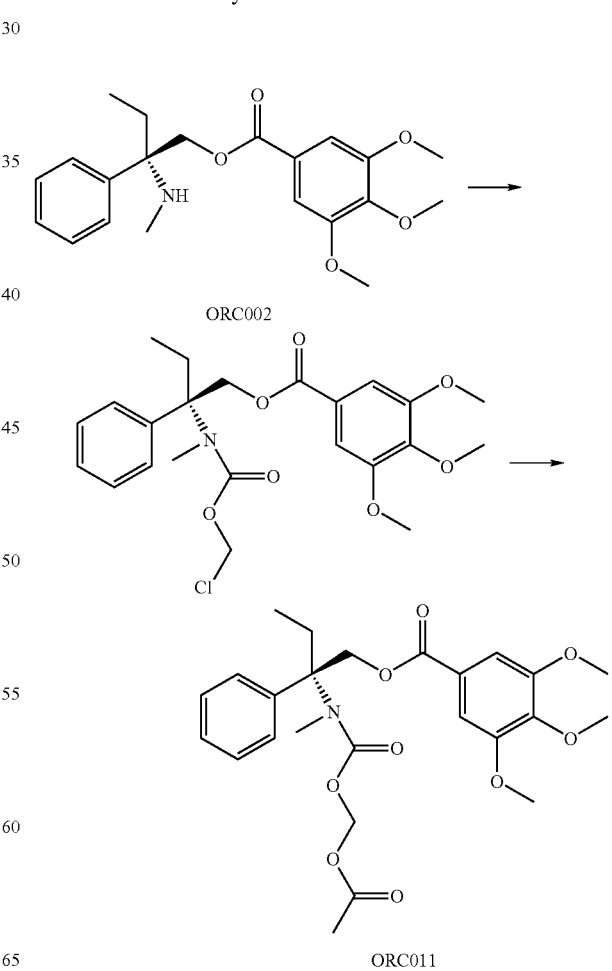

Stage 1:

1.17 g (2.83 mmol; 1 eq.) of (S) 2-methylamino-2-phenyl-n-butyl 3,4,5-trimethoxybenzoate is placed under nitrogen then solubilized in 1 ml of 1,2-dichloroethane. 0.77 ml (8.50 mmol; 3 eq.) of chloromethyl chloroformate is then added slowly, dropwise. The reaction mixture is stirred for 6 hours at ambient temperature then treated with 0.10 ml saturated NaHCO$_3$ then extracted with 20 ml dichloromethane. The organic phase is again washed with 10 ml saturated NaHCO$_3$, dried over Na$_2$SO$_4$, filtered then evaporated to dryness.

The residue obtained is purified by flash chromatography on silica gel (ethyl acetate/cyclohexane 2:8, v/v) in order to produce 0.830 g (63%) of the expected product (S) 2-(chloromethoxycarbonyl methyl amino)-2-phenyl-n-butyl 3,4,5-trimethoxybenzoate in the form of a colourless oil.

$^1$H-NMR (CDCl$_3$, 400 MHz): δ (ppm)=0.92 (t, J=7.2 Hz, 3H, CH$_3$); 2.24 (m, 1H, diastereotopic CH$_2$); 2.45 (m, 1H, diastereotopic CH$_2$); 3.03 (s(b), 3H, NCH$_3$); 3.89 (s, 6H, 2×OCH$_3$); 3.91 (s, 3H, OCH$_3$); 4.99 (s(b), 2H, OCH$_2$); 5.71 (s(b), 2H, ClCH$_2$); 7.19-7.37 (m, 7H, ArH). MS (CI, NH$_3$): m/z (%)=483 [(M+NH$_4$)$^+$, 65], 465 [(M$^+$.), 10], 343 [(MH-C$_3$O$_2$NClH$_5$)$^+$, 100]. R$_f$ (SiO$_2$, ethyl acetate/cyclohexane, 3:7): 0.41

Stage 2:

0.289 g (0.62 mmol; 1 eq.) of (S) 2-(chloromethoxycarbonyl methyl amino)-2-phenyl-n-butyl 3,4,5-trimethoxybenzoate are placed in solution in 10.2 ml N,N-dimethylformamide then placed at 0° C. Then a whitish suspension of 0.125 g of (0.62 mmol; 1 eq.) caesium acetate in 4.1 ml N,N-dimethylformamide is slowly added. Stirring is maintained for 17 hours at ambient temperature. Then an additional 0.038 g (0.18 mmol; 0.3 eq.) of caesium acetate is added and stirring is continued for 7 hours at ambient temperature.

The reaction mixture is then diluted in 20 ml of ethyl acetate. The organic phase is washed with 2×12 ml of NaHCO$_3$ (10%), 2×12 ml of water and 12 ml of saturated NaCl, dried over Na$_2$SO$_4$, filtered and evaporated to dryness. The residue obtained is purified by flash chromatography on silica gel (ethyl acetate/cyclohexane gradient 1:9 to 3:7, v/v) in order to produce 0.065 g (20%) of the expected product (S) 2-(acetoxymethoxycarbonyl methyl amino)-2-phenyl-n-butyl 3,4,5-trimethoxybenzoate in the form of a colourless oil.

$^1$H-NMR (CDCl$_3$, 400 MHz): δ (ppm)=0.80 (t, J=6.5 Hz, 3H, CH$_3$); 1.92 (s, 3H, CH$_3$CO); 2.13 (s(b), 1H, diastereotopic CH$_2$); 2.35 (m, 1H, diastereotopic CH$_2$); 2.93 (s(b), 3H, NCH$_3$); 3.80 (s, 6H, 2×OCH$_3$); 3.82 (s, 3H, OCH$_3$); 4.82 (d, J=10.6 Hz, 1H, diastereotopic CH$_2$); 4.96 (m, 1H, diastereotopic OCH$_2$); 5.57 (s(b), 2H, OCH$_2$O); 7.10-7.27 (m, 7H, ArH). MS (CI, NH$_3$): m/z (%)=479 [(M+NH$_4$—C$_2$H$_5$)$^+$, 100], 285 [15], 230 [15].

R$_f$(SiO$_2$, ethyl acetate/cyclohexane 3:7):0.21.

Example 3

Synthesis of ORC007

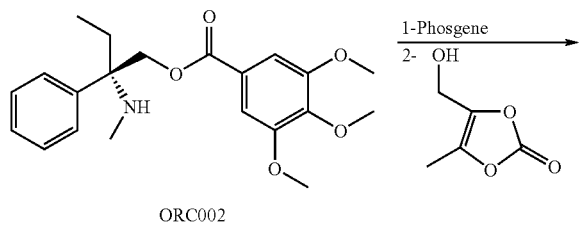

ORC002

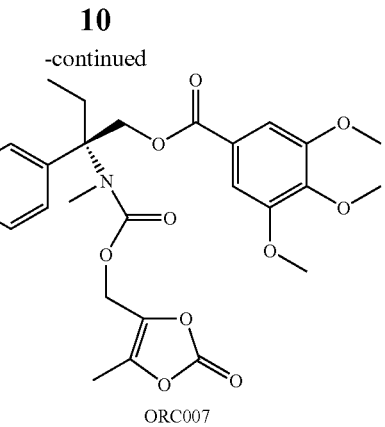

ORC007

0.40 g (1.07 mmol; 1 eq.) of (S) 2-methylamino-2-phenyl-n-butyl 3,4,5-trimethoxybenzoate is placed under nitrogen then placed in solution in 53 ml of dichloromethane. Then 1.3 ml (2.53 mmol; 2.36 eq.) of a solution at 20% of phosgene in toluene is added, then 0.16 ml (1.18 mmol; 1.1 eq.) of triethylamine. Stirring is maintained for 22 hours at ambient temperature. 0.69 g (5.35 mmol; 5 eq.) of 4-(hydroxymethyl)-5-methyl-1,3-dioxol-2-one is then added. After an additional 24 hours at ambient temperature, the reaction mixture is washed with 2×40 ml water and 1×40 ml of 1M HCl. The organic phase is dried over Na$_2$SO$_4$, filtered then evaporated to dryness.

The residue obtained is purified by 2 flash chromatographies on silica gel (dichloromethane then ethyl acetate/cyclohexane gradient 1:9 to 3:7, v/v) in order to produce 0.085 g (15%) of the expected product (S) 2-(5-methyl-1,3-dioxol-2-one-4-yl methyl amino)-2-phenyl-n-butyl 3,4,5-trimethoxybenzoate in the form of a colourless oil.

$^1$H-NMR (CDCl$_3$, 400 MHz):

δ(ppm)=0.78 (t, J=7.2 Hz, 3H, CH$_3$); 1.94 (s, 3H, CH$_3$); 2.02 (m, 1H, diastereotopic CH$_2$); 2.32 (m, 1H, diastereotopic CH$_2$); 3.02 (s(b), 3H, NCH$_3$); 3.80 (s, 6H, 2×OCH$_3$); 3.82 (s, 3H, OCH$_3$); 4.64 (s(b), 2H, OCH$_2$Csp$_2$); 4.80 (m, 1H, diastereotopic OCH$_2$); 4.93 (m, 1H, diastereotopic OCH$_2$); 7.10-7.27 (m, 7H, ArH).

MS (CI, NH$_3$): m/z (%)=547 [(M+NH$_4$)$^+$, 5], 479 [80], 260 [100].

R$_f$(SiO$_2$, dichloromethane/methanol, 98:2): 0.16.

Example 4

Synthesis of ORC020

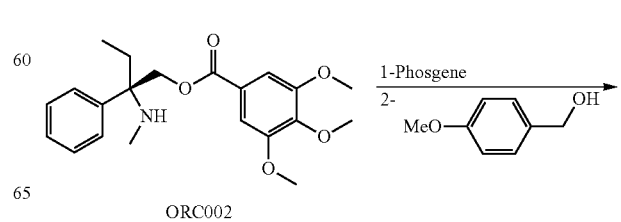

ORC002

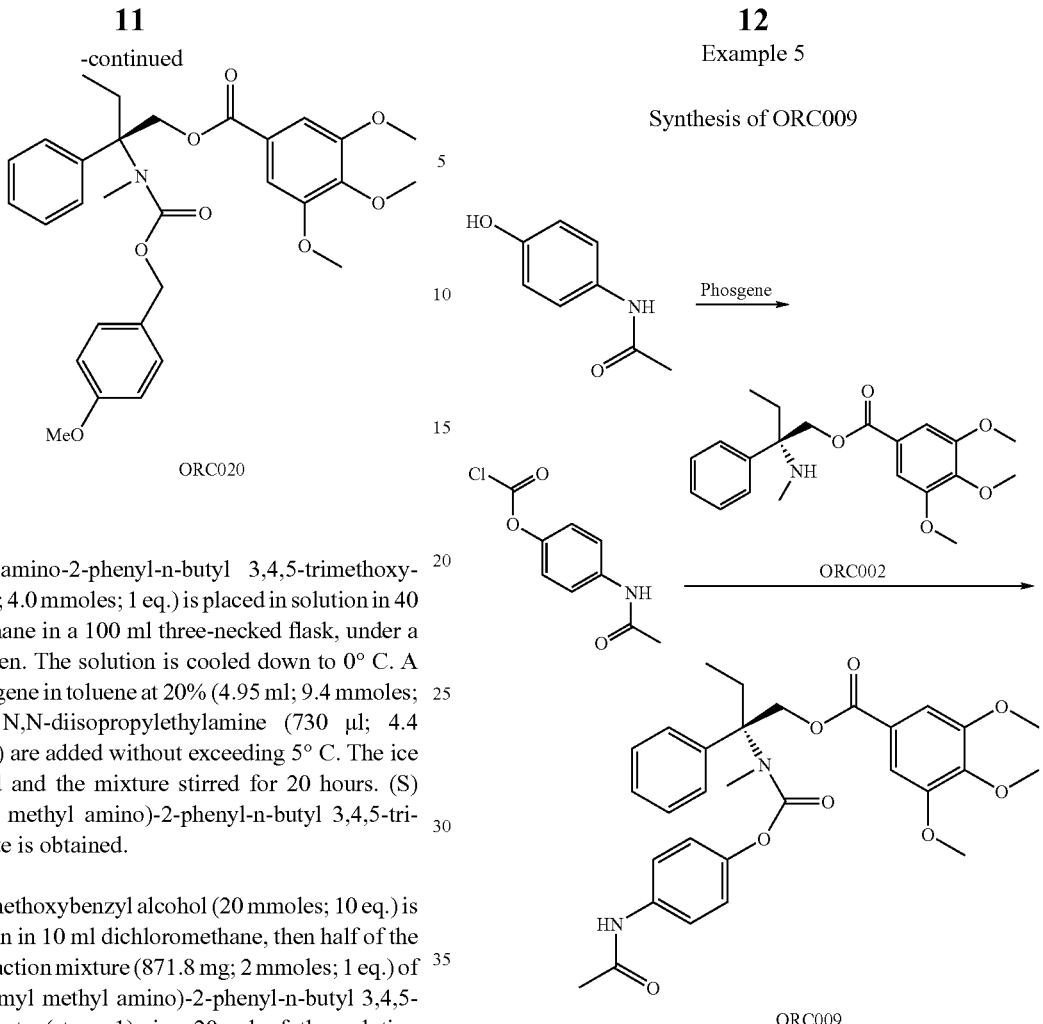

ORC020

Stage 1:

(S) 2-methylamino-2-phenyl-n-butyl 3,4,5-trimethoxybenzoate (1.49 g; 4.0 mmoles; 1 eq.) is placed in solution in 40 ml dichloromethane in a 100 ml three-necked flask, under a stream of nitrogen. The solution is cooled down to 0° C. A solution of phosgene in toluene at 20% (4.95 ml; 9.4 mmoles; 2.4 eq.) then N,N-diisopropylethylamine (730 µl; 4.4 mmoles; 1.1 eq.) are added without exceeding 5° C. The ice bath is removed and the mixture stirred for 20 hours. (S) 2-(chloroformyl methyl amino)-2-phenyl-n-butyl 3,4,5-trimethoxybenzoate is obtained.

Stage 2:

2.53 ml of 4-methoxybenzyl alcohol (20 mmoles; 10 eq.) is placed in solution in 10 ml dichloromethane, then half of the volume of the reaction mixture (871.8 mg; 2 mmoles; 1 eq.) of (S) 2-(chloroformyl methyl amino)-2-phenyl-n-butyl 3,4,5-trimethoxybenzoate (stage 1), i.e. 20 ml of the solution obtained, is added dropwise. After 1 hour at ambient temperature, N,N-diisopropylethylamine (1.30 ml; 8 mmoles; 4 eq.) is added, then stirring is maintained for 20 hours. The reaction mixture is poured into 20 ml of a saturated solution of $NH_4Cl$ (pH=7-8). After decantation, the aqueous phase is extracted with 2×20 ml of dichloromethane. The organic phases are combined and washed with 2×20 ml of a saturated solution of $NH_4Cl$ (pH=7 then pH=6), and 20 ml of a semi-saturated solution of NaCl then dried with $Na_2SO_4$. The crude product is purified on silica gel of (35 parts, eluent ethyl acetate/cyclohexane 7/3 in order to obtain a transparent oil of (S) 2-(4-methoxybenzyloxycarbonyl methyl amino)-2-phenyl-n-butyl 3,4,5-trimethoxybenzoate (15%; 170 mg). The oil is taken up in 1 ml of ether and 1 ml of pentane in order to have an emulsion which remains. The flask is cooled for 2 hours at 4° C. then the solvent supernatant is removed using a Pasteur pipette. The solid is dried using a vane pump in order to produce a white foam.

$R_f$ ($SiO_2$, ethyl acetate/cyclohexane 7:3): 0.42

$^1$H-NMR ($CDCl_3$, 400 MHz):

δ (ppm)=0.86 (t, J=7.3 Hz, 3H); 2.16 (qd, J=7.3 Hz and 14.8 Hz, 1H, $CH_2$); 2.38 (qd, J=7.3 Hz and 14.8 Hz, 1H, $CH_2$); 3.09 (bs, 3H); 3.80 (s, 3H); 3.87 (s, 6H); 3.91 (s, 3H); 4.93 (ml, 4H); 6.79 (m, 2H); 7.05 (ml, 1H); 7.18 (m, 2H); 7.30 (m, 6H).

MS (CI, $NH_3$): m/z=555 [(M+$NH_4$)$^+$], 537, 494, 463, 268.

Example 5

Synthesis of ORC009

0.081 g (0.54 mmol; 1 eq.) of 4-acetamidophenol under nitrogen is placed in suspension in 3.6 ml of dry ethyl acetate and placed at 0° C. Then 0.43 ml (0.82 mmol; 1.54 eq.) of a 20% solution of phosgene in toluene is added. Then (still at 0° C.) 0.075 ml (0.54 mmol; 1 eq.) of triethylamine is added. Then it is placed at ambient temperature. After 1 hour, 0.40 g (1.07 mmol; 2 eq.) of (S) 2-methylamino-2-phenyl-n-butyl 3,4,5-trimethoxybenzoate is added. Stirring is continued for 18 hours at ambient temperature. The reaction mixture is diluted in 5 ml ethyl acetate then washed with 8 ml of water and 8 ml of 1M HCl. The organic phase is dried over $Na_2SO_4$, filtered, then evaporated to dryness.

The residue obtained is purified by flash chromatography on silica gel (dichloromethane to dichloromethane/methanol gradient 9:1, v/v). The product obtained is triturated twice in 1.5 ml of pentane/ether 1:1 in order to produce 0.092 g (31%) of a white solid (S) 2-(4-acetylaminophenyloxycarbonyl methylamino)-2-phenyl-n-butyl 3,4,5-trimethoxybenzoate.

$^1$H-NMR ($CDCl_3$, 400 MHz): δ (ppm)=0.86 (t, J=6.8 Hz, 3H, $CH_3$); 2.02 (s, 3H, $CH_3CO$); 2.18 (m, 1H, diastereotopic $CH_2$); 2.43 (m, 1H, diastereotopic $CH_2$); 3.06 (s(b), 3H, $NCH_3$); 3.79 (s, 6H, 2×$OCH_3$); 3.83 (s, 3H, $OCH_3$); 4.87 (d, J=11.1 Hz, 1H, diastereotopic $CH_2$); 5.03 (m, 1H, diastereotopic $CH_2$); 6.70 (s(b), 1H, NH); 7.14-7.37 (m, 11H, ArH).

MS (CI, $NH_3$): m/z (%)=568 [(M+NH4)$^+$, 90], 374 [(MH—$C_9O_3NH_8$)$^+$, 10], 343 [(MH—$C_{10}O_3N_2H_{11}$)$^+$, 40].

$R_f$ ($SiO_2$, dichloromethane/methanol 98:2): 0.28

Example 6

Synthesis of ORC021

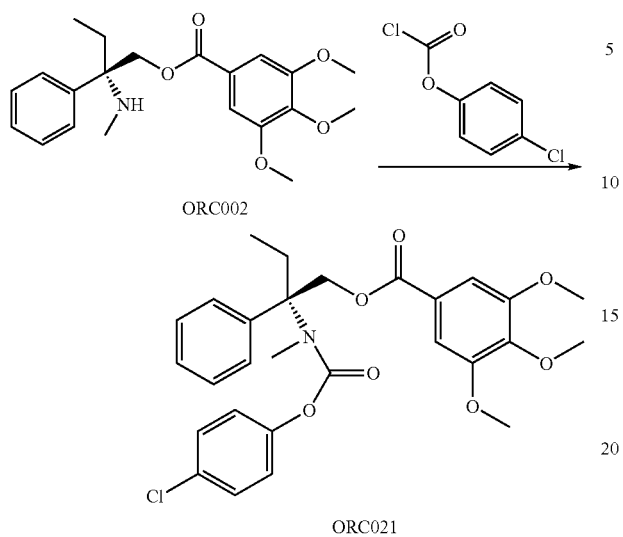

400 µl (2.4 mmoles; 3 eq.) of DIPEA is added dropwise at ambient temperature under nitrogen to the solution of 300 mg (0.8 mmoles; 1 eq.) of (S) 2-methylamino-2-phenyl-n-butyl 3,4,5-trimethoxybenzoate in 3 ml of dichloromethane, then 337 µl (2.4 mmoles; 3 eq.) of 4-chlorophenyl chloroformate are added dropwise. The mixture is stirred at ambient temperature for 70 hours. The reaction mixture is poured into 30 ml of saturated NaHCO$_3$ (pH=7), then extracted with 30 ml of dichloromethane, then 10 ml of dichloromethane. The organic phase is washed with 20 ml of saturated NaCl (pH=7-8) then dried over Na$_2$SO$_4$ and evaporated to dryness in order to produce an oil. The latter is purified on a column of silica gel (50 parts; eluent ethyl acetate/cyclohexane 2/8). The oil obtained is cooled down to −50° C. under nitrogen in order to precipitate the product, 2×2 ml pentane are added. The product is then dried under vacuum for 1 hour in order to produce a white powder containing 4% solvent that cannot be evaporated off. The powder is solubilized in 1 ml of CH$_2$Cl$_2$ then evaporated to dryness in order to produce a white foam of (S) 2-(4-chlorophenoxycarbonyl methyl amino)-2-phenyl-n-butyl 3,4,5-trimethoxybenzoate (360 mg, 85%) after pumping for 20 hours.

R$_f$ (SiO$_2$, ethyl acetate/cyclohexane 4:6): 0.66

$^1$H-NMR (CDCl$_3$, 400 MHz):

δ (ppm)=0.94 (t, J=7.4 Hz, 3H); 2.27 (m, 1H, CH$_2$); 2.51 (qd, J=7.4 Hz and 14.6 Hz, 1H, CH$_2$); 3.20 (bs, 3H); 3.88 (s, 6H); 3.92 (s, 3H); 5.00 (dd, J=10.4 Hz and J=61.1 Hz, 2H, CH$_2$); 6.80 (bs, 2H); 7.23 (bm, 3H); 7.29 (m, 2H); 7.38 (m, 4H).

MS (CI, NH$_3$): m/z=545 [(M+NH$_4$)$^+$], 343, 195.

Example 7

Synthesis of ORC018

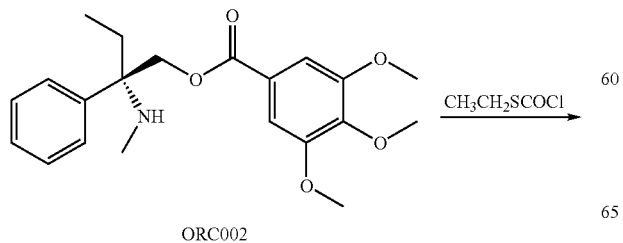

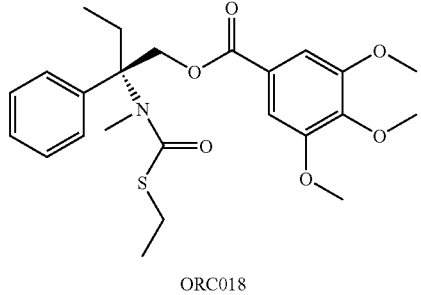

N,N-diisopropylethylamine (0.4 ml; 2.4 mmoles; 3 eq.) is added at ambient temperature dropwise under nitrogen to a solution of (S) 2-methylamino-2-phenyl-n-butyl 3,4,5-trimethoxybenzoate (300 mg; 0.8 mmoles; 1 eq.) in dichloroethane, then ethyl chlorothioformate (260 µl; 2.4 mmoles; 3 eq.) is added dropwise. Stirring is maintained at ambient temperature for 70 hours. The reaction mixture is poured into 30 ml of saturated NaHCO$_3$ (pH=7), then extracted with 30 ml of dichloromethane and 10 ml of dichloromethane. The organic phase is washed with 20 ml of saturated NaCl (pH=7-8) then dried over Na$_2$SO$_4$ and evaporated to dryness. The oil obtained is dissolved in 3 ml of ether, then under gentle heating, 3 ml of pentane is added dropwise. The cloudy solution is kept cold for 20 hours then the supernatant is removed with a pipette. The operation is carried out twice with 5 ml of ether/pentane. Then the crystals are dried in the flask in order to obtain a white powder of (S) 2-(ethylthiocarbonyl methyl amino)-2-phenyl-n-butyl 3,4,5-trimethoxybenzoate (251 mg, 68%).

R$_f$ (SiO$_2$, ethyl acetate/cyclohexane 1:3): 0.50.

$^1$H-NMR (CDCl$_3$, 400 MHz): δ (ppm)=0.93 (t, J=7.4 Hz, 3H); 1.24 (t, J=7.3 Hz, 3H); 2.22 (qd, J=7.4 Hz and 14.3 Hz, 1H, CH$_2$); 2.41 (qd, J=7.4 Hz and 14.3 Hz, 1H, CH$_2$); 2.83 (q, J=7.3 Hz, 2H); 3.02 (s, 3H); 3.88 (s, 6H); 3.90 (s, 3H); 4.99 (d, J=11.3 Hz, 1H, CH$_2$); 5.11 (d, J=11.3 Hz, 1H, CH$_2$); 7.16 (bs, 2H); 7.26 (m, 1H); 7.34 (m, 4H).

MS (CI, NH$_3$): m/z=479 [(M+NH$_4$)$^+$], 462 [(M+H)$^+$], 343, 250.

Example 8

ORC033

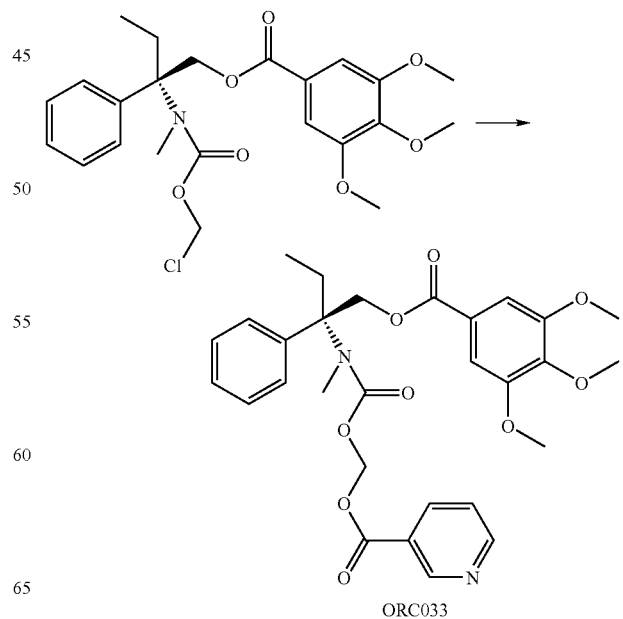

Nicotinic acid (0.081 g, 0.00064 mol) is solubilized in DMF (1 mL) under a nitrogen atmosphere. Caesium fluoride (0.098 g, 0.00064 mol) is added and the solution is stirred at ambient temperature for 15 minutes. The solution is cooled down to 0° C. and (S) 2-(chloromethoxycarbonyl methyl amino)-2-phenyl-n-butyl 3,4,5-trimethoxybenzoate (100.0 mg, 0.0002146 mol), previously solubilized in DMF (1 mL) is added dropwise. The mixture is heated at 70° C. for 17 hours.

After cooling, ethyl acetate (5 mL) is added and the organic phase is washed with a saturated solution of NaHCO3 then with a saturated solution of sodium chloride. The organic phase is dried over Na2SO4, filtered and evaporated in order to produce 120 mg of a yellow oil. The product is purified [(SiO2; cyclohexane/AcOEt (3/7)] in order to produce 86 mg of (S)-2-(nicotinyloxy-methoxycarbonyl methyl amino)-2-phenyl-n-butyl 3,4,5-trimethoxy-benzoate as an amorphous white solid.

TLC: SiO2, cyclohexane/AcOEt (3/7) Rf 0.37

NMR 1H (CDCl$_3$): δ 0.86 (3H, t, J=7.55 Hz, CH3-CH2), 2.10-2.22 (1H, m, CH—CH3), 2.40-2.48 (1H, m, CH—CH3), 3.09 (3H, br s, NCH3), 3.85-3.88 (9H, d, J=9.79 Hz, 3 OCH3), 4.88-4.95 (2H, br d, J=9.61 Hz, CH2-O), 5.91 (2H, br s, CH2), 7.14 (2H, s, H$_{arom}$), 7.25-7.39 (8H, m, H$_{arom}$), 8.20 (1H, br s, Hpyr), 8.77-8.80 (1H, dd, J1=1.69 Hz, J2=4.89 Hz, Hpyr), 9.15 (1H, br s, Hpyr).

MS (ES+): [M+H]+, m/z: 552

Example 9

ORC035

N-carbobenzyloxyglycine (0.20 g, 0.00096 mol) is solubilized in DMF (2 mL) under a nitrogen atmosphere. Sodium fluoride (0.15 g, 0.00096 mol) is added and the mixture is stirred for 15 minutes at ambient temperature.

The mixture is cooled down to 0° C. and (S) 2-(chloromethoxycarbonyl methyl amino)-2-phenyl-n-butyl 3,4,5-trimethoxybenzoate (150.0 mg, 0.0003219 mol) in solution in DMF (2 mL) is added dropwise. The reaction mixture is stirred at 70° C. for 2 hours. After cooling, ethyl acetate (8 mL) is added and the organic phase is washed with a saturated aqueous solution of sodium bicarbonate (3 mL), then a saturated solution of sodium chloride (3 mL), then the organic phase is dried over Na2SO4, filtered then evaporated in order to produce a yellow oil. The product is purified: SiO2, cyclohexane/AcOEt (7/3 then 6/4) in order to produce 197 mg of 3,4,5-trimethoxy-benzoic acid (S)-2-[(2-benzyloxycarbonylamino-acetoxymethoxycarbonyl)-methyl-amino]-2-phenyl-butyl ester as a yellow oil.

TLC: SiO2, cyclohexane/AcOEt (3/7) Rf 0.50

NMR $^1$H(CDCl$_3$): δ (ppm)=0.85 (3H, t, J=7.53 Hz, CH$_3$—CH$_2$), 2.08-2.27 (1H, m, CH—CH$_3$), 2.36-2.46 (1H, m, CH—CH$_3$), 3.05 (3H, br s, NCH$_3$), 3.85-3.90 (9H, d, J=8.29 Hz, 3 OCH$_3$), 4.86 (2H, br s, CH$_2$—O), 5.11-5.20 (4H, m, 2 CH2), 5.70 (2H, br s, CH$_2$), 7.16 (2H, s, H$_{arom}$), 7.25-7.40 (10H, m, H$_{arom}$)

MS (ES+) [M+Na]+, m/z: 638

Example 10

ORC036

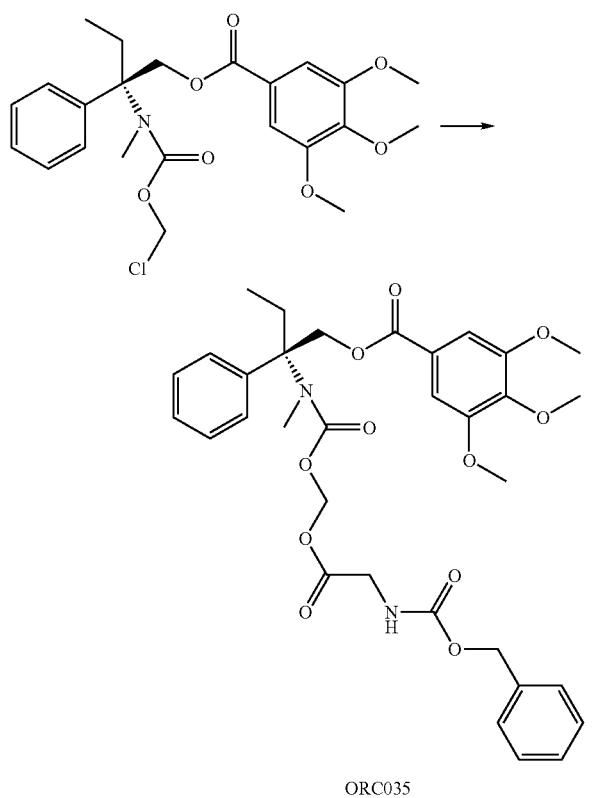

ORC035

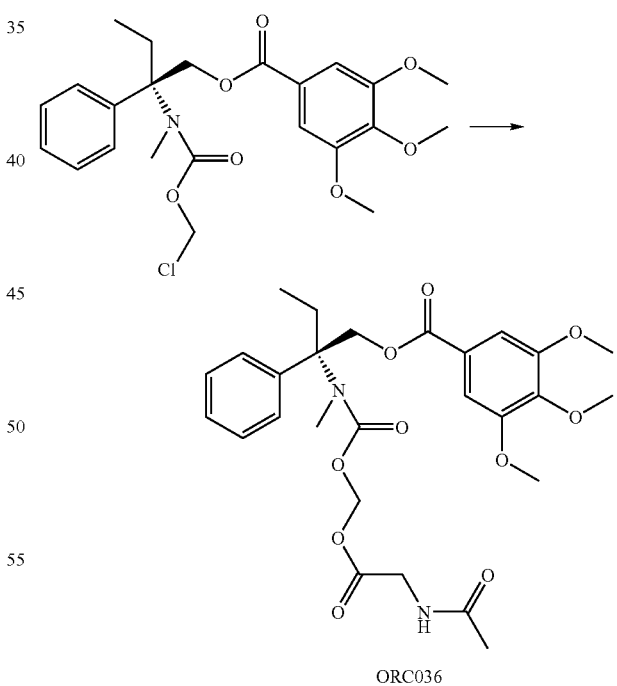

ORC036

N-acetyl-glycine (0.075 g, 0.00064 mol) is solubilized in DMF (1 mL, 0.01 mol) under a nitrogen atmosphere. Caesium fluoride (0.098 g, 0.00064 mol) is added and the mixture is stirred for 15 minutes at ambient temperature. The mixture is cooled down to 0° C. and (S) 2-(chloromethoxycarbonyl methyl amino)-2-phenyl-n-butyl 3,4,5-trimethoxybenzoate (100.0 mg, 0.0002146 mol) in solution in DMF (1 mL) is added dropwise. The reaction mixture is heated at 70° C. for 17 hours.

After cooling, ethyl acetate (5 mL) is added and the organic phase is washed with a saturated aqueous solution of sodium bicarbonate, then a saturated aqueous solution of sodium chloride (2 mL), finally dried over Na2SO4, filtered and evaporated in order to produce 3,4,5-trimethoxy-benzoic acid (S)-2-[(2-acetylamino-acetoxymethoxycarbonyl)-methyl-amino]-2-phenyl-butyl ester as a yellow oil (205 mg).

TLC: SiO2, cyclohexane/AcOEt (1/9) Rf 0.34

NMR 1H (CDCl3): δ (ppm)=0.86 (3H, t, J=7.34 Hz, CH3-CH2), 2.04 (3H, s, CH3-CO), 2.18-2.26 (1H, m, CH—CH3), 2.32-2.57 (1H, m, CH—CH3), 3.05 (3H, br s, NCH3), 3.86-3.90 (9H, d, J=6.97 Hz, 3 OCH3), 3.96 (2H, br s, CH2), 4.83-4.90 (1H, br d, J=10.54 Hz, CH—O), 5.03-5.06 (1H, br s, CH—O), 5.66-5.74 (2H, br s, CH2), 5.91-5.95 (1H, br s), 7.17 (2H, s, $H_{arom}$), 7.24-7.37 (5H, m, $H_{arom}$).

MS (ES+) [M+Na]+, m/z: 546

Example 11

ORC037

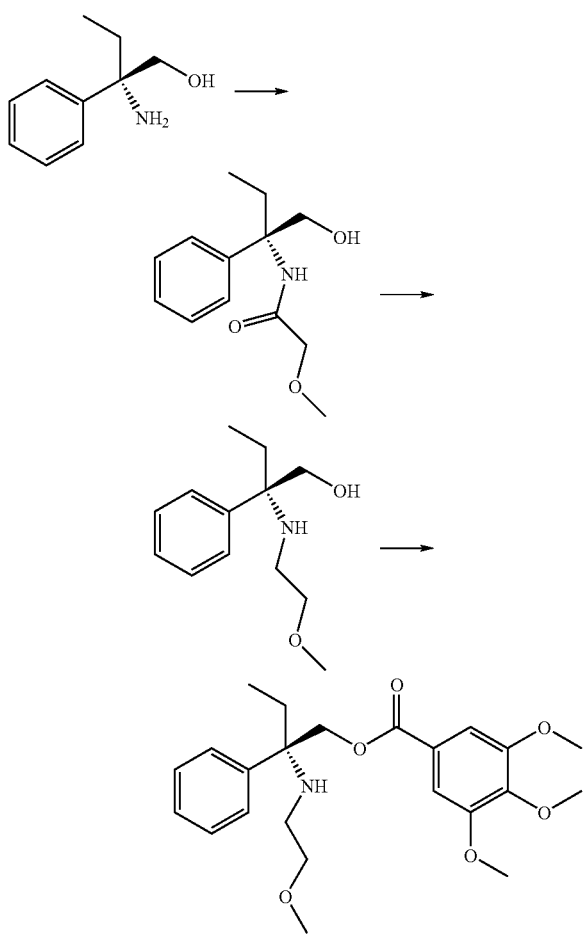

ORC037

Stage 1:

(S)-2-amino-2-phenyl-butan-1-ol (15.0 g, 0.0908 mol) is solubilized in methylene chloride (150 mL) under a nitrogen atmosphere. 1-hydroxybenzotriazole (13.5 g, 0.0998 mol), methoxyacetic acid (7.82 mL, 0.0998 mol) and N-(3-dimethylaminopropyl)-N'-ethylcarbodiimide hydrochloride (19.5 g, 0.0998 mol) are added. The resulting colourless solution is stirred at ambient temperature for 4 days.

The mixture is washed with 0.1N HCl (100 mL) and then a saturated solution of sodium chloride (100 mL). The organic phase is dried over Na2SO4, filtered and concentrated in order to produce 22.4 g of an orange oil, which is chromatographed: SiO2, CH2Cl2/MeOH (99/1 and 98/2) in order to produce 13.12 g of a slightly yellow solid.

NMR $^1$H (CDCl$_3$): δ 0.83 (3H, t, J=7.34 Hz, CH$_3$—CH$_2$), 1.97-2.18 (2H, m, CH$_2$—CH$_3$), 3.49 (3H, s, OCH$_3$), 3.82-4.10 (4H, m, 2 CH$_2$), 5.03 (1H, t, J=6.78 Hz, OH), 7.09 (1H, br s, NH), 7.28-7.42 (5H, m, $H_{arom}$).

Stage 2:

13.120 g, 0.055290 mol (N—((S)-1-hydroxymethyl-1-phenyl-propyl)-2-methoxy-acetamide) is solubilized in THF (100 mL), under a nitrogen atmosphere. The solution is cooled down to 10° C., then borane-dimethyl sulphide complex (16 mL, 0.16 mol) is added dropwise. The mixture is stirred at ambient temperature for 2 days. 70 mL methanol is added slowly and the solution is stirred for 15 minutes. 100 mL of a 10% potassium carbonate solution, then 400 mL of ethyl acetate are added. The organic phase is washed with a saturated solution of sodium chloride (100 mL), dried over Na2SO4, filtered then evaporated in order to produce 12.4 g of a yellow oil.

NMR $^1$H(CDCl$_3$): δ (ppm)=0.69 (3H, t, J=7.34 Hz, CH$_3$—CH$_2$), 1.73-1.82 (1H, m), 1.90-2.01 (1H, m), 2.53-2.67 (2H, m, CH$_2$), 3.30 (3H, s, OCH$_3$), 3.48 (2H, m, CH2), 3.86-3.98 (2H, dd, J$_1$=10.90 Hz, J$_2$=15.07 Hz), 7.24-7.40 (5H, m, $H_{arom}$).

Stage 3:

12.40 g (0.05553 mol), ((S)-2-(2-methoxy-ethylamino)-2-phenyl-butan-1-ol) is introduced into a flask equipped with a distillation bend, then solubilized in a toluene (400 mL)/ethanol (20 mL) mixture. 18.71 g (0.08107 mol) of the methyl ester of 3,4,5-trimethoxy-benzoic acid is added. The solution is then heated to 130° C. 1.5 g, 0.028 mol of sodium methylate is added by portions at 130° C. The white suspension obtained is stirred at 130° C. for 17 hours. 1.0 g of sodium methylate is again added by portions at 130° C. and the suspension is stirred for an another 3 hours.

After cooling, the reaction mixture is evaporated then taken up with a 3N solution of NaOH (200 mL). The mixture is stirred for 15 minutes, then extracted with ethyl acetate (300 mL). The organic phase is washed with a saturated solution of sodium chloride (200 mL), dried over Na2SO4, filtered and evaporated in order to produce 18.6 g of an orange oil. The product is purified: SiO2, CH2Cl2 then CH2Cl2/MeOH (95/5) in order to produce 8.3 g of 3,4,5-trimethoxy-benzoic acid (S)-2-(2-methoxy-ethylamino)-2-phenyl-butyl ester as a yellow oil.

TLC: SiO2, CH2Cl2/MeOH (95/5) Rf 0.41

NMR 1H(CDCl3): δ (ppm)=0.80 (3H, t, J=7.34 Hz, CH3-CH2), 1.82-1.93 (2H, m), 2.51-2.57 (1H, m), 2.64-2.72 (1H, m), 3.31 (3H, s, OCH3), 3.46-3.51 (2H, m, CH2), 3.85-3.90 (9H, d, J=8.47 Hz, 3 OCH3), 4.51-4.67 (2H, dd, J1=11.11 Hz, J2=24.30 Hz), 7.21-7.53 (7H, m, H arom).

MS (ES+) [M+H]+, m/z: 417

(S) 2-amino-2-phenyl-n-butanol can be prepared according to the method described in applications FR 2765218 and EP 510168.

Example 12

ORC050

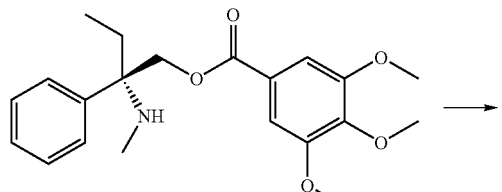

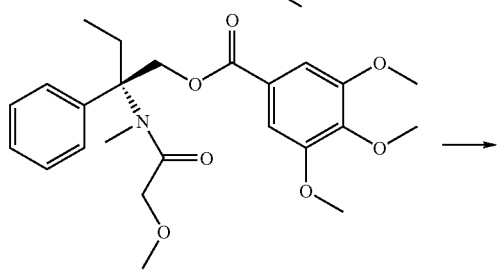

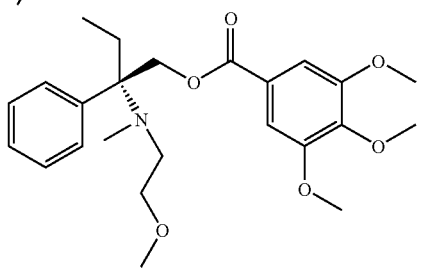

ORC050

Stage 1:

(S)-2-methylamino-2-phenyl-butyl ester of 3,4,5-trimethoxy-benzoic acid (2.0 g, 0.0054 mol), is solubilized in methylene chloride (20 mL) under a nitrogen atmosphere. 1-hydroxybenzotriazole (796 mg, 0.00589 mol), methoxyacetic acid (541 mg, 0.00589 mol) and N-(3-dimethylaminopropyl)-N'-ethylcarbodiimide hydrochloride (1150 mg, 0.00589 mol) are added. The colourless solution is stirred at 40° C. for 2 days. The mixture is washed with 0.1N hydrochloric acid (20 mL), then with a saturated solution of sodium chloride (20 mL). The organic phase is dried over Na2SO4, filtered and evaporated in order to produce 1.84 g of a yellow oil. The product is purified: SiO2, cyclohexane/AcOEt (1/1) in order to produce 796 mg of a yellow oil.

TLC: SiO2, cyclohexane/AcOEt (1/1) Rf 0.65

NMR 1H (CDCl3): δ (ppm)=0.91 (3H, t, J=7.34 Hz, CH3-CH2), 2.18-2.26 (1H, m), 2.38-2.46 (1H, m), 2.94 (3H, s, NCH3), 3.41 (3H, s, OCH3), 3.85-3.90 (9H, d, J=9.79 Hz, 3 OCH3), 4.09 (2H, br s, CH2), 4.99 (1H, d, J=11.49 Hz), 5.25 (1H, d, J=11.49 Hz), 7.11 (2H, s, H arom), 7.21-7.39 (5H, m, H arom).

Stage 2:

335 mg of the previous product is solubilized in THF (1 mL). 0.28 mL (0.0030 mol) of borane-dimethyl sulphide complex is added dropwise and the mixture is stirred at ambient temperature for 3 days. Methanol (0.7 mL) is added to the reaction mixture and the solution is stirred for 30 minutes. A 10% potassium carbonate solution (1 mL) and then 3 mL of ethyl acetate (3 mL) are added. The organic phase is washed with a saturated solution of sodium chloride (1 mL), dried over Na2SO4, filtered and evaporated in order to produce 135 mg of a slightly yellow oil. The product is purified: SiO2, cyclohexane/AcOEt (7/3) in order to produce 221 mg of 3,4,5-trimethoxy-benzoic acid (S)-2-[(2-methoxy-ethyl)-methyl-amino]-2-phenyl-butyl ester as a colourless oil.

NMR 1H (CDCl3): δ (ppm)=0.68 (3H, t, J=7.34 Hz, CH3—CH2), 1.87 (2H, q, J=7.35 Hz, CH2—CH3), 2.44 (3H, s, NCH3), 2.84 (2H, t, J=6.59 Hz, CH2), 3.28 (3H, s, OCH3), 3.44 (2H, t, J=6.59 Hz), 3.82-3.90 (9H, d, J=16.58 Hz, 3 OCH3), 4.75-4.84 (2H, dd, J1=3.77 Hz, J2=11.87 Hz, CH2), 7.21-7.50 (7H, m, $H_{arom}$).

MS (ES+) [M+H]+, m/z: 431

Example 13

ORC051

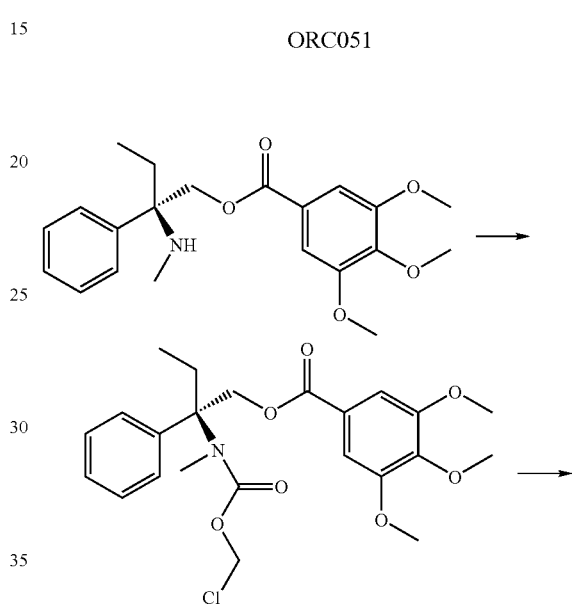

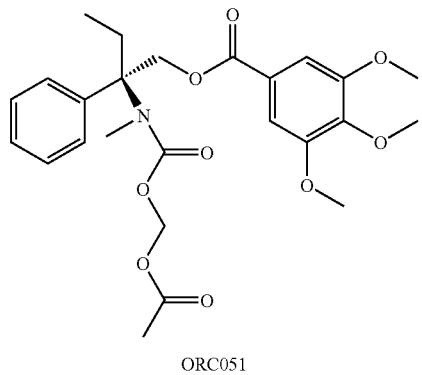

ORC051

Stage 1:

200.0 mg (0.0005356 mol) of (R) 2-(chloromethoxycarbonyl methyl amino)-2-phenyl-n-butyl 3,4,5-trimethoxybenzoate is solubilized in methylene chloride (1.0 mL) under a nitrogen atmosphere. The colourless solution is cooled down to −1° C. and chloromethyl chloroformate (210 mg, 0.0016 mol) is added dropwise. The reaction mixture is stirred at ambient temperature for 17 hours. The colourless solution is then cooled down to −5° C. and chloromethyl chloroformate (0.106 mg, 1.5 eq) is again added dropwise. The solution is stirred at ambient temperature for 3 hours. The mixture is cooled down to 0° C. and chloromethyl chloroformate (106 mg, 1.5 eq) is again added dropwise. The solution is stirred at ambient temperature for 2 hours, then heated at 40° C. for 1 hour, then stirred at ambient temperature for 15 hours.

The organic phase is treated with a saturated solution of bicarbonate (3.0 mL), after having added 3 mL of methylene chloride. The organic phase is washed with a saturated solution of sodium chloride (3.0 mL), dried over Na2SO4, filtered then evaporated in order to produce 150 mg of a slightly yellow oil.

NMR 1H (CDCl$_3$): δ (ppm)=0.90 (3H, t, J=7.34 Hz, CH$_3$—CH$_2$), 2.17-2.24 (1H, m, CH—CH$_3$), 2.36-2.46 (1H, m, CH—CH$_3$), 3.01 (3H, br s, NCH$_3$), 3.87-3.89 (9H, d, J=5.84 Hz, 3 OCH$_3$), 4.93-4.97 (2H, br d, J=10.55 Hz, CH$_2$—O), 5.69 (2H, br s, CH$_2$—Cl), 7.17 (2H, s, H$_{arom}$), 7.25-7.36 (5H, m, H$_{arom}$).

Stage 2:

3,4,5-trimethoxy-benzoic acid (R)-2-(chloromethoxycarbonyl-methyl-amino)-2-phenyl-butyl ester (150.0 mg, 0.0003219 mol) is solubilized in DMF (2.0 mL) under a nitrogen atmosphere. The solution is cooled down to 0° C. and sodium acetate (195 mg, 0.000965 mol) solubilized in DMF (2.0 mL) is added dropwise. The mixture is heated at 70° C. for 15 hours. After cooling, ethyl acetate (13.0 mL) and a saturated solution of bicarbonate (13.0 mL) are added.

The mixture is stirred for 15 minutes at ambient temperature. The organic phase is washed with a saturated solution of sodium chloride (10 mL), dried over NaSO4, filtered then evaporated in order to produce a yellow oil. The product obtained is purified through a column: SiO2, Cyclohexane/AcOEt (8/2) in order to produce, after evaporation, 116 mg of 3,4,5-trimethoxy-benzoic acid (R)-2-(acetoxymethoxycarbonyl-methyl-amino)-2-phenyl-butyl ester as a yellow oil.

TLC: SiO2, Cyclohexane/AcOEt (1/1) Rf: 0.64

NMR 1H (CDCl3): δ (ppm)=0.87 (3H, t, J=7.34 Hz, CH3—CH2), 1.99 (3H, br s, CH3—CO), 2.14-2.23 (1H, m, CH—CH3), 2.40-2.47 (1H, m, CH—CH3), 3.01 (3H, br s, NCH3), 3.87-3.89 (9H, d, J=5.65 Hz, 3 OCH3), 4.87-4.92 (2H, br d, J=10.73 Hz, CH2-O), 5.65 (2H, br s, CH2—Cl), 7.17 (2H, s, H arom), 7.25-7.36 (5H, m, H arom).

MS (ES+) [M+NH4]+, m/z: 507

Example 14

ORC 052

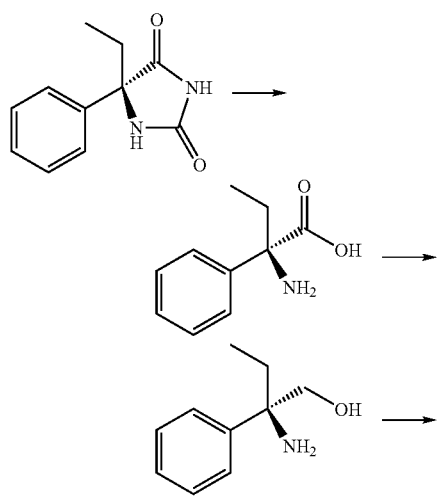

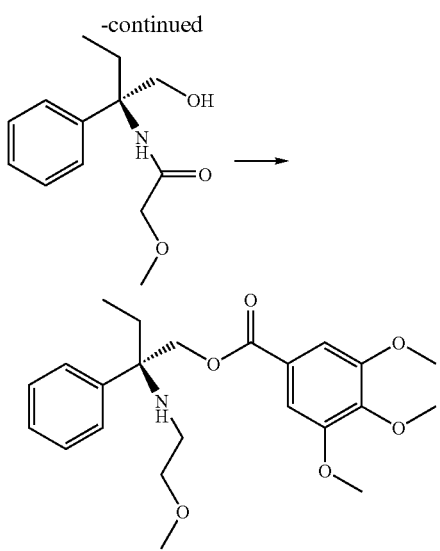

ORC052

Stage 1:

In an autoclave, sodium hydroxide (17.120 g, 0.42803 mol) is solubilized in water (74 mL, 4.1 mol), then (5R)-5-ethyl-5-phenylimidazolidine-2,4-dione (20.0 g, 0.0979 mol) is added in portions. The reaction mixture is heated at 130° C. under stirring for 48 hours. The mixture is cooled down and a white precipitate forms.

The pH is adjusted to 7 then the precipitate is washed with ethyl acetate. The mixture is diluted in 300 mL water cooled down to 0° C. The pH is adjusted to 1 with 12 M HCl (50.0 mL). The precipitate is completely dissolved. While maintaining the mixture at 0° C., the pH is adjusted to 7 with 20 mL of a 5N NaOH solution in order to obtain a white precipitate. The mixture is filtered, the precipitate is washed with water (150 mL) then dried under vacuum at 40° C. in order to produce 22.8 g of a white solid.

NMR $^1$H (MeOD): δ (ppm)=1.06 (3H, t, J=7.34 Hz, CH$_3$—CH$_2$), 2.30-2.38 (2H, m, CH$_2$—CH$_3$), 7.33-7.46 (3H, m, H$_{arom}$), 7.55-7.59 (2H, m, H$_{arom}$).

Stage 2:

(2R)-2-amino-2-phenylbutanoic acid (21.60 g, 0.1205 mol) is solubilized in THF (200 mL) under a nitrogen atmosphere. Borane-THF 1M in solution in THF (94 mL, 0.96 mol) is added dropwise. The mixture is heated at 70° C. under stirring for 48 hours. Borane-THF 1M in solution in THF (47 mL, 4 eq) is added dropwise. The mixture is heated at 70° C. for 2 hours. The operation is repeated.

The mixture is finally cooled down to 0° C. then a saturated solution of sodium bicarbonate (100.0 mL) is added. After the addition of methylene chloride, the organic phase is washed with a saturated solution of sodium chloride, finally dried over Na2SO4, then filtered and evaporated in order to produce 13.06 g of a slightly yellow solid.

NMR 1H (MeOD): δ (ppm)=0.59 (3H, t, J=7.34 Hz, CH$_3$—CH$_2$), 1.57-1.69 (1H, m, CH—CH$_3$), 1.71-1.84 (1H, m, CH—CH$_3$), 3.52-3.61 (2H, dd, J$_1$=10.92 Hz, J$_2$=4.14 Hz, CH$_2$—OH), 7.09-7.33 (5H, m, H$_{arom}$).

Stage 3:

(2R)-2-amino-2-phenyl-butan-1ol (13.060 g, 0.079040 mol) is solubilized in methylene chloride (300 mL) under a nitrogen atmosphere. Methoxy acetic acid (7.99 g, 0.0869 mol), 1-hydroxybenzotriazole (11.8 g, 0.0870 mol) and N-(3-dimethylaminopropyl)-N'-ethylcarbodiimide, (HCl) (16.70 g, 0.08537 mol) are added directly to the mixture with a minimum amount of methylene chloride. The solution is stirred at ambient temperature for 17 hours. The mixture is washed with 0.1 M HCl (300.0 mL). The aqueous phase is extracted with methylene chloride (3 times 200.0 mL).

The organic phases are combined, washed with a saturated solution of sodium chloride (600.0 mL), dried over Na2SO4, filtered, then evaporated in order to produce 14 g of a yellow oil. The product is purified: SiO2, CH2Cl2/MeOH (99/1, 98/2, 100% MeOH) in order to produce 5.17 g of a slightly yellow oil.

NMR 1H (CDCl$_3$): δ (ppm)=0.83 (3H, t, J=7.34 Hz, CH$_3$—CH$_2$), 1.96-2.16 (2H, m, CH$_2$—CH$_3$), 3.49 (3H, s, OCH$_3$), 3.82-4.10 (4H, m, 2 CH$_2$), 5.03 (1H, t, J=6.78 Hz, OH), 7.09 (1H, br s, NH), 7.26-7.42 (5H, m, H$_{arom}$)

Stage 4:

N-(1-hydroxymethyl-1-phenyl-propyl)-2-methoxy-acetamide (5.170 g, 0.02179 mol) is solubilized in THF (50.0 mL) under a nitrogen atmosphere. The solution is cooled down to 10° C., then borane-dimethyl sulphide complex (6.2 mL, 0.065 mol) is added dropwise. The mixture is stirred at ambient temperature for 24 hours. The solution is cooled down to 10° C., then borane-dimethyl sulphide complex (6.2 mL, 3 eq) is added dropwise. The mixture is stirred at ambient temperature for 3 hours. The mixture is then cooled down to 0° C. and methanol (27.0 mL) is added dropwise. 40 mL of a 10% potassium carbonate solution, then 80 mL of ethyl acetate are added to the mixture. The aqueous phase is extracted with ethyl acetate. The organic phase is washed with a saturated solution of sodium chloride, dried over Na2SO4, filtered then evaporated in order to produce 4.92 g of a yellow oil.

NMR 1H (CDCl$_3$): δ (ppm)=0.66 (3H, t, J=7.34 Hz, CH$_3$—CH$_2$), 1.53-1.69 (1H, m), 1.73-1.89 (1H, m), 2.40-2.60 (2H, m, CH$_2$), 3.36 (3H, s, OCH$_3$), 3.43-3.48 (2H, m, CH$_2$), 3.72-3.88 (2H, dd, J$_1$=10.90 Hz, J$_2$=15.07 Hz), 7.21-7.40 (5H, m, H$_{arom}$).

Stage 5:

(2R)-2-(2-methoxy-ethylamino)-2-phenyl-butan-1-ol (4.840 g, 0.02167 mol) is solubilized in a Toluene (150 mL)/methanol (7.60 mL) mixture in a flask equipped with a distillation bend. The methyl ester of 3,4,5-trimethoxy-benzoic acid (5.50 g, 0.0238 mol) is added and the mixture is heated to 130° C. Sodium methylate (0.58 g, 0.011 mol) is added in portions and the mixture is stirred at 130° C. for 3 hours.

Sodium methylate (0.47 g, 0.0087 mol) is again added in portions and the mixture is stirred at 130° C. for 15 hours. The mixture is cooled down then evaporated. 70 mL of a 3M aqueous solution of sodium hydroxide are added then the mixture is stirred for 15 minutes before being extracted with ethyl acetate. The organic phase is washed with a saturated solution of sodium chloride, dried over Na2SO4, filtered, then evaporated in order to produce 8.87 g of an orange oil. The product is purified through a column: SiO2, Cyclohexane/AcOEt (9/1, 8/2) then 100% AcOEt) in order to produce 4.37 g of 3,4,5-trimethoxy-benzoic acid (R)-2-(2-methoxy-ethylamino)-2-phenyl-butyl ester as a slightly yellow oil.

TLC: SiO2 CH2Cl2/MeOH (95/5); Rf: 0.34

NMR 1H (CDCl3), δ (ppm)=0.80 (3H, t, J=7.34 Hz, CH3-CH2), 1.79-1.95 (2H, m), 2.50-2.57 (1H, m), 2.64-2.72 (1H, m), 3.31 (3H, s, OCH3), 3.46-3.51 (2H, m, CH2), 3.86-3.89 (9H, d, J=8.28 Hz, 3 OCH3), 4.51-4.67 (2H, dd, J1=1.11 Hz, J2=24.30 Hz), 7.21-7.53 (7H, m, H arom).

MS (ES+) [M+H]+, m/z: 417.

Example 15

ORC055

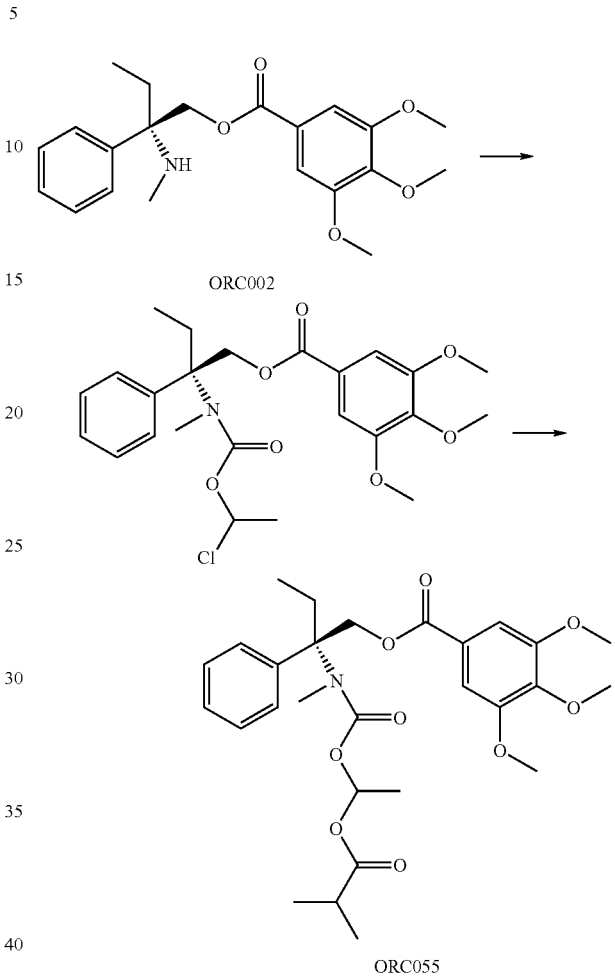

Stage 1:

500 mg (1.34 mmol; 1.0 eq.) of (S) 2-methylamino-2-phenyl-n-butyl 3,4,5-trimethoxybenzoate is dissolved in 1 ml of dichloromethane under nitrogen. The mixture is cooled down to 2° C. A this temperature, 440 μl (4.0 mmol; 3.0 eq.) of α-chloroethyl chloroformate are added dropwise. The mixture is stirred at ambient temperature for 5 hours. The reaction is monitored by TLC. The dichloromethane is evaporated off under nitrogen. The residue obtained in the form of a colourless oil is used in the following stage without additional purification.

$^1$H-NMR (CDCl$_3$, 300 MHz): δ (ppm)=0.94 (m, 3H, CH$_3$); 1.59 (m, 3H, CH$_3$); 2.22 (m, 1H, diastereotopic CH$_2$); 2.45 (m, 1H, diastereotopic CH$_2$); 3.08 (br, 3H, NCH$_3$); 3.90 (s, 3H, OCH$_3$); 3.91 (s, 3H, OCH$_3$); 3.92 (s, 3H, OCH$_3$); 5.00 (br, 2H, OCH$_2$); 6.48 (br, 1H, ClCH); 7.19-7.39 (m, 7H, ArH).

R$_f$ (SiO$_2$, Cyclohexane/Ethyl acetate, 6/4): 0.8

Stage 2:

(S) 2-[(1-chloro-ethoxycarbonyl)-methyl-amino]-2-phenyl-n-butyl 3,4,5-trimethoxy-benzoate obtained in the previous stage is dissolved in 2 mL of N,N-dimethylformamide. 807 mg (3.67 mmol, 2.7 eq.) of caesium isobutyrate is added. The mixture is stirred at 55° C. overnight. The reaction is monitored by TLC.

10 ml water is added to the mixture. The product is extracted with ethyl acetate (3 times 10 mL) then the organic phase is washed successively with water and a saturated solution of sodium chloride (15 mL). The organic phases are dried over $Na_2SO_4$, filtered then concentrated to dryness in order to produce a brown oil. The oil is purified by flash chromatography on silica gel (eluent: cyclohexane/ethyl acetate: 85/15) in order to produce 105 mg of the expected product (S) 2-[(1-isobutyryloxy-ethoxycarbonyl)-methyl-amino]-2-phenyl-n-butyl 3,4,5-trimethoxy-benzoate in the form of a colourless oil (yield=15%).

1H-NMR (CDCl3, 300 MHz): δ (ppm)=0.91 (m, 3H, CH3 ethyl); 1.10 (m, 6H, 2×CH3 isopropyl); 2.2 (br, 2H, CH2 ethyl); 2.4 (br, 3H, CH3CH); 3.05 (br, 4H, CH3N+CH isopropyl); 3.89 (s, 6H, CH3O); 3.89 (s, 6H, CH3O); 3.91 (s, 3H, CH3O); 4.89-4.98 (br, 2H, OCH2); 6.71 (br, 1H, OCHO); 7.17-7.39 (m, 7H, ArH).

Rf (SiO2, cyclohexane/ethyl acetate, 6/4): 0.9
MS (ES+) [M+NH4]+, m/z: 549.2

Example 16

ORC056

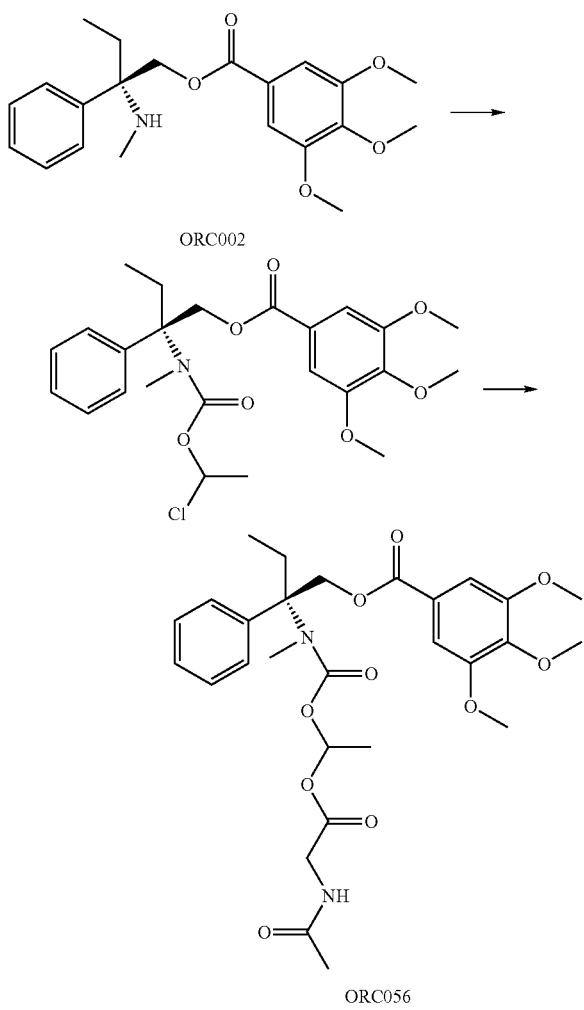

Stage 1:

2 g (5.4 mmol; 1.0 eq.) of (S) 2-methylamino-2-phenyl-n-butyl 3,4,5-trimethoxybenzoate is dissolved in 4 ml dichloromethane under nitrogen. The mixture is cooled down to 2° C. At this temperature, 884 µl (8.0 mmol; 1.5 eq.) of α-chloroethyl chloroformate is added dropwise. The mixture is stirred at ambient temperature for 5 hours. The reaction is monitored by TLC. The dichloromethane is evaporated off under nitrogen. The residue obtained in the form of a colourless oil is used in the following stage without additional purification.

$^1$H-NMR (CDCl$_3$, 300 MHz): δ (ppm)=0.94 (m, 3H, CH$_3$); 1.59 (m, 3H, CH$_3$); 2.22 (m, 1H, diastereotopic CH$_2$); 2.45 (m, 1H, diastereotopic CH$_2$); 3.08 (br, 3H, NCH$_3$); 3.90 (s, 3H, OCH$_3$); 3.91 (s, 3H, OCH$_3$); 3.92 (s, 3H, OCH$_3$); 5.00 (br, 2H, OCH$_2$); 6.48 (br, 1H, ClCH); 7.19-7.39 (m, 7H, ArH).

R$_f$ (SiO$_2$, cyclohexane/ethyl acetate, 6/4): 0.8

Stage 2:

The (S) 2-[(1-chloro-ethoxycarbonyl)-methyl-amino]-2-phenyl-n-butyl 3,4,5-trimethoxy-benzoate obtained in the previous stage is dissolved in 3 mL of N,N-dimethylformamide. 2.0 g (8.03 mmol, 1.5 eq.) of caesium (acetylamino) acetate is added. The mixture is stirred at 55° C. overnight. The reaction is monitored by TLC.

20 ml water is added to the mixture. The product is extracted with ethyl acetate (3 times 50 mL) then the organic phase is washed successively with water and a saturated solution of sodium chloride (10 mL). The organic phases are dried over Na$_2$SO$_4$, filtered then concentrated to dryness in order to produce a brown oil. The oil is purified by flash chromatography on silica gel (eluent: cyclohexane/ethyl acetate: 3/7) in order to produce 200 mg of the expected product (S) 2-{[1-(2-acetylamino-acetoxy)-ethoxycarbonyl]-methyl-amino}-2-phenyl-n-butyl 3,4,5-trimethoxy-benzoate in the form of a brown solid (yield=7%).

1H-NMR (CDCl3, 300 MHz): δ (ppm)=0.81 (m, 3H, CH3 ethyl); 1.94 (s, 3H, CH3CO); 2.15 (m, 2H, CH2 ethyl); 2.35 (m, 3H, CH3CH); 3.0 (br, 3H, CH3N); 3.90 (m, 9H, OCH3); 4.80 (m, 2H, OCH2); 5.95 (br, 2H, CH2N); 6.65 (br, 1H, OCHO); 7.10-7.30 (m, 7H, ArH).

Rf (SiO2, cyclohexane/ethyl acetate, 3/7): 0.2
[M+NH4]+, m/z: 578.2

The products of general formula (I) can be administered by oral, parenteral, perlingual, rectal route, in aerosols or in topical form. The present invention also relates to pharmaceutical compositions comprising at least one 2-amino-2-phenyl-alkanol ester derivative of general formula (I) and/or their salts, when they exist, in the pure state or in a combined form with one or more compatible and pharmaceutically acceptable diluents or adjuvants.

These compositions can be presented in the form of solid compositions, in particular in the form of tablets, coated tablets, of pills, gelatin capsules, powders to be placed in solution or in suspension, or granules, or in the form of liquid compositions such as injectable solutions or suspensions, drinkable solutions or suspensions, syrups, emulsions, elixirs containing diluents such as water or paraffin oil or in the form of suppositories, creams, ointments and lotions or also in the form of spray compositions. These pharmaceutical forms are prepared according to the usual methods. In the solid compositions for oral administration the active ingredient according to the invention is mixed with one or more inert diluents or adjuvants, such as for example saccharose, lactose, starch or its derivatives, microcrystalline cellulose, colloidal silica, povidone, talc, gum arabic. These compositions can comprise substances other than diluents, for example a lubricant such as magnesium stearate or a coating intended for controlled release.

The liquid compositions liquids for oral administration can comprise aqueous or non-aqueous vehicles such as diluents and can also comprise other substances such as for example wetting agents, sweeteners or flavourings. The non-aqueous compositions can comprise fatty substances of animal or vegetable origin, paraffin derivatives, glycols, soya lecithin.

The compositions which can be administered by parenteral route are more particularly compositions which can be administered by intramuscular or intravenous route. The compositions for parenteral administration can be sterile solutions or emulsions. As a solvent or vehicle, propylene glycol, a polyethylene glycol, vegetable oils, in particular olive oil, injectable organic esters, for example ethyl oleate, can be used. These compositions can also contain adjuvants, in particular wetting, isotonic, emulsifying, dispersant and stabilizing agents and/or preservatives.

Sterilisation can be carried out in several ways, for example using a bacteriological filter, by irradiation or by heating. The compositions can also be prepared in the form of sterile solid compositions which are dissolved in sterile water or any other sterile injectable medium at the time of use.

Compositions for rectal administration are suppositories or rectal capsules, containing, apart from the active ingredient, excipients such as cocoa butter, semi-synthetic glycerides or polyethylene glycols. Compositions for topical administration can be for example patches containing compatible excipients such as silicone oil, paraffin, as well as the active ingredient.

The compositions can also be aerosols. For use in the form of liquid aerosols, the compositions can be stable sterile solutions or solid compositions dissolved at the time of use in non-pyrogenic sterile water, serum or any other pharmaceutically acceptable vehicle. For use in the form of dry aerosols intended to be directly inhaled, the active ingredient is comminuted and combined with a diluent or hydrosoluble solid vehicle having a grain size of 30 to 80 pm, for example dextran, mannitol or lactose.

In human therapeutics, the medical practitioner will determine the dosage regime deemed most suitable in relation to the treatment, according to the age, weight and other factors pertaining to the patient to be treated. The usual dose, variable according to the patient treated and the disorder in question, can be for example 50 mg to 2 g per day for an adult, by oral route.

The following example illustrates a composition according to the invention.

EXAMPLE

A formulation is prepared which can be administered by oral route, having the following composition:

| | |
|---|---|
| (S) 2-(chloromethoxycarbonyl methyl amino)-2-phenyl-n-butyl 3,4,5-trimethoxybenzoate | 100 mg |
| lactose monohydrate, | |
| modified maize starch, | |
| hydroxypropyl methylcellulose, | |
| sodium carboxymethyl starch, | |
| tartaric acid, | |
| colloidal silica, | |
| magnesium stearate, | |
| macrogol 4000, | |
| titanium dioxide. | |

The invention claimed is:

1. A compound represented by formula (I):

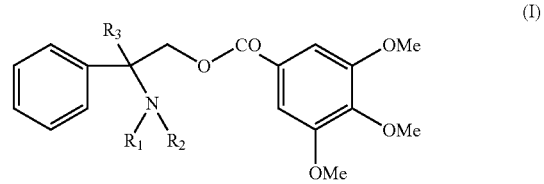

in which:
R$_1$ is a hydrogen atom, an alkyl radical having 1 to 4 carbon atoms in a straight or branched chain, an alkyl radical having 2 to 4 carbon atoms in a straight or branched chain substituted by hydroxy, alkoxy, alkylthio, acyloxy, amino, alkylamino, dialkylamino, alkylcarbamoyloxy, alkoxycarbonylamino, ureido or alkylureido, R$_2$ is a —CO—R radical in which R is an alkyl radical, an aryl, or benzyl, a —CO—Y—R$_4$ radical for which Y is a heteroatom chosen from —O—, —S—, —NH—, -Nalk- for which alk is a straight or branched alkyl radical having 1 to 4 carbon atoms, and R$_4$ is chosen from an alkyl radical, an aryl radical, and an aralkyl radical, capable of being substituted by one or more halogen atoms or hydroxy, alkyl radicals having from 1 to 4 carbon atoms in a straight or branched chain, alkoxy, alkylthio, acylaminoalkylthio, alkoxycarbonyl or acylamino, the alkyl residues of which have 1 to 4 carbon atoms in a straight or branched chain, or oxo, or capable of being substituted by a R$_5$COO— radical having R$_5$ that is an alkyl radical optionally substituted by benzyloxycarbonylamino, acylamino or by an amino acid residue, or an alkyl radical having 2 to 4 carbon atoms substituted by hydroxy, alkoxy, alkylthio, acyloxy, amino, alkylamino, or dialkylamino, it being understood that said substituted alkyl radical is in a straight or branched chain and has at least 2 carbon atoms between the nitrogen atom bearing R$_2$ and the substituent;

R$_3$ is an alkyl radical having 1 to 4 carbon atoms in a straight or branched chain, in their R or S forms or their mixtures, as well as their pharmaceutically acceptable salts, when these exist.

2. A compound according to claim 1, wherein R$_2$ in —NR$_1$R$_2$ is a —CO—O—R$_4$ radical for which R$_4$ has a structure:

$$C(alk)\text{-}O\text{—}CO\text{—}R_5 \qquad (X)$$

alk being an alkyl radical having 1 to 6 carbon atoms in a straight or branched chain and R$_5$ is defined as in claim 1, or wherein R$_1$ is a hydrogen atom and R$_2$ is a —CO—R radical.

3. A compound according to claim 2, wherein R$_1$ is a hydrogen atom, an alkyl radical having 1 to 4 carbon atoms, or a 2-methoxyethyl radical.

4. A compound according to claim 1, wherein R$_2$ in —NR$_1$R$_2$ is a substituted alkyl radical.

5. A composition comprising a 3,4,5-trimethoxy-benzoic acid (S)-2-[(2-acetylamino-acetoxymethoxycarbonyl)-methyl-amino]-2-phenyl-butyl ester.

6. A composition comprising a (S)-2-[(1-isobutyryloxy-ethoxycarbonyl)-methyl-amino]-2-phenyl-n-butyl 3,4,5-trimethoxy-benzoate.

7. A composition comprising a (S)-2-{[1-(2-acetylamino-acetoxy)-ethoxycarbonyl]-methyl-amino}-2-phenyl-n-butyl 3,4,5-trimethoxy-benzoate.

8. A composition comprising a 3,4,5-trimethoxy-benzoic acid (S)-2-(2-methoxy-ethylamino)-2-phenyl-butyl ester.

9. A composition comprising a 3,4,5-trimethoxy-benzoic acid (S)-2-[(2-methoxy-ethyl)-methyl-amino]-2-phenyl-butyl ester.

10. A method for the preparation of a compound as defined in claim 1, comprising reacting a compound represented by formula (II):

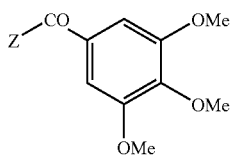
(II)

in which Z is a halogen atom, a hydroxy radical or the residue of a reactive ester, with a 2-amino-2-phenyl alkanol represented by formula (III):

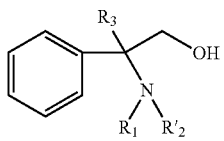
(III)

in which $R_1$ and $R_3$ are defined as previously and $R'_2$ is a hydrogen atom or is defined as $R_2$ in claim 1, wherein when one of $R'_2$ or $R_1$ is the hydrogen atom, by substitution of the amine of the 2-amino-2-phenyl-alkanol ester obtained, represented by formula (IV):

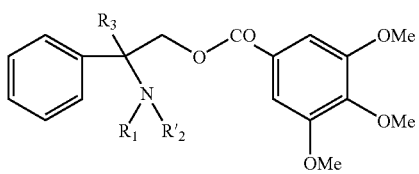
(IV)

in which $R_1$ and $R'_2$ and $R_3$ are defined as above;
either, when $R'_2$ is H, to obtain compounds for which $R_2$ is —CO—R, by the action of a halide or a reactive ester of the acid represented by formula (V):

R—COOH (V)

or, when $R'_2$ is H, to obtain compounds for which $R_2$ is —CO—Y—$R_4$, Y being O, S, NH or Nalk,
either, by the action of phosgene, followed by reaction with the alcohol or thiol represented by formula (VI):

$R_4$—YH (VI)

in which $R_4$ is an optionally substituted alkyl radical or an aryl or an aralkyl radical, and Y is the oxygen or the sulphur atom, or a NH or Nalk radical,
or, by the action of the halide represented by formula (VII):

$R_4$—Y—COHal (VII)

in which $R_4$ is defined as in claim 1, Y is the oxygen or sulphur atom and Hal is a halogen atom,
or, to obtain an $R_4$ radical bearing the —C(alk)—O—CO—$R_5$ substitution for which alk is an alkyl radical having 1 to 6 carbon atoms in a straight or branched chain and $R_5$ is defined as in claim 1, by the action of chloroalkylchloroformate, followed by reacting the product obtained with an alkaline salt of the corresponding acid $R_5$COOH, or alternatively the silver salt or the quaternary ammonium salt of said acid;
either, when $R'_2$ is H, to obtain compounds for which $R_2$ is substituted alkyl, or when a compound represented by formula (IV) has been obtained, for which $R_1$ is a hydrogen atom and $R'_2$ is defined as $R_2$ in claim 1, to obtain a product represented by formula (I) for which $R_1$ is optionally substituted alkyl, by acylation by an acid halide or a reactive ester structure represented by formulas (VIIIa) or (VIIIb):

$R_2$—CO—Z (VIIIa)

or $R_1$—CO—Z (VIIIb)

in which $R_1$ or $R_2$ are defined as above and Z is a halogen atom or the residue of a reactive ester, followed by reduction of the amide formed to an amine,
or also, when a compound represented by formula (IV) has been obtained for which $R_1$ is a hydrogen atom and $R'_2$ is defined as $R_2$ in claim 1, and to obtain a product represented by formula (I) for which $R_1$ is alkyl, by the action of a halogenated compound represented by formula (IX):

$R_1$—X (IX)

in which $R_1$ is an alkyl radical and X is a halogen atom or a sulphonic radical, in the presence of a base, then optionally the product obtained is converted to a pharmaceutically acceptable salt, when these exist.

11. A pharmaceutical composition comprising at least one compound of claim 1, in the pure state or in a combination with one or more compatible and pharmaceutically acceptable diluents or adjuvants.

12. The compound according to claim 3, wherein $R_1$ is a methyl group.

13. A method according to claim 10, wherein $R_4$ is a branched alkyl group.

14. A method according to claim 10, wherein Hal is chlorine.

* * * * *